United States Patent
Portman

(10) Patent No.: US 11,718,878 B2
(45) Date of Patent: Aug. 8, 2023

(54) EXOSOME PROFILING FOR DIAGNOSIS AND MONITORING OF VASCULITIS AND VASCULOPATHIES INCLUDING KAWASAKI DISEASE

(71) Applicant: Seattle Children's Hospital, Seattle, WA (US)

(72) Inventor: Michael Portman, Mercer Island, WA (US)

(73) Assignee: Seattle Children's Research Hospital, Seattle, WA (US)

( * ) Notice: Subject to any disclaimer, the term of this patent is extended or adjusted under 35 U.S.C. 154(b) by 310 days.

(21) Appl. No.: 16/640,323

(22) PCT Filed: Aug. 20, 2018

(86) PCT No.: PCT/IB2018/056292
§ 371 (c)(1),
(2) Date: Feb. 19, 2020

(87) PCT Pub. No.: WO2019/038660
PCT Pub. Date: Feb. 28, 2019

(65) Prior Publication Data
US 2020/0248260 A1  Aug. 6, 2020

Related U.S. Application Data

(60) Provisional application No. 62/548,330, filed on Aug. 21, 2017.

(51) Int. Cl.
*C12Q 1/6883* (2018.01)

(52) U.S. Cl.
CPC ..... *C12Q 1/6883* (2013.01); *C12Q 2600/178* (2013.01); *G01N 2800/328* (2013.01)

(58) Field of Classification Search
None
See application file for complete search history.

(56) References Cited

U.S. PATENT DOCUMENTS

| | | |
|---|---|---|
| 2009/0304680 A1 | 12/2009 | Kuijpers et al. |
| 2010/0184046 A1* | 7/2010 | Klass .................... C12Q 1/6811 435/7.1 |
| 2016/0108368 A1 | 4/2016 | Larocca et al. |
| 2016/0333408 A1* | 11/2016 | Jia ......................... C12Q 1/6883 |
| 2018/0185417 A1* | 7/2018 | Joly ....................... A61K 35/12 |
| 2018/0224465 A1 | 8/2018 | Goetzl |
| 2018/0231558 A1* | 8/2018 | Lyden .............. G01N 33/57438 |

FOREIGN PATENT DOCUMENTS

WO  WO 2016/201129 A1  12/2016

OTHER PUBLICATIONS

Jiang (Experimental and Therapeutic Medicine vol. 14 pp. 3159-3164, pub online Aug. 8, 2017).*
Li (PNAS Jan. 21, 2014 vol. 111 No. 3 pp. 1002-1007).*
Panwar (Bioinformatics 33(10), 2017 pp. 1554-1560).*
Washietl (Genome Research 24:616-628 2014).*
Kuo (Pediatrics and Neonatology 2012 53, 4-11).*
Huang (Oncotarget, 2017, vol. 8, No. 7 pp. 11249-11258 published Jan. 4, 2017).*
Li, Zhonghan et al., "The long noncoding RNA THRIL regulates TNFα expression through its interaction with hnRNPL" PNAS, Jan. 2014, pp. 1002-1007, vol. 111, No. 3.
International Search Report for PCT/IB2018/056292 dated Nov. 30, 2018.
Sharma et al., 2018, Methods to enrich exosomes from conditioned media and biological fluids, Methods Mol Biol. 1710:103-115.

* cited by examiner

*Primary Examiner* — Amanda Haney
(74) *Attorney, Agent, or Firm* — Knobbe, Martens, Olson & Bear, LLP

(57) ABSTRACT

Some embodiments of the methods and compositions provided herein relate to the detection of biomarkers for Kawasaki disease (KD), the diagnosis of KD in a subject, and/or the amelioration or treatment of KD in a subject. In some embodiments, a biomarker can include a long intergenic non-coding RNA (lincRNA). In some embodiments, the biomarker can be present in an exosome-enriched serum sample from a subject.

18 Claims, 3 Drawing Sheets

Specification includes a Sequence Listing.

```
SEQUENCE LISTING

<160> NUMBER OF SEQ ID NOS: 22

<210> SEQ ID NO 1
<211> LENGTH: 410
<212> TYPE: DNA
<213> ORGANISM: homo sapiens

<400> SEQUENCE: 1
gctaattttt aaattttag tagagacggg gttttgaact cctggtctcc aacgcctgac      60
ctcaagtgat ccacccgcct cagcctccca aagtgctaag attacagctc gtgttcttca    120
gttgtcttcc ctacgctgct gcctcggcag tcactatctc ctcaggaagc agtcccaccc    180
gcccctttct cttccacggc atccacacca tccggatgcc tggattcaaa tgccacgtca    240
ccacttgcca gctgcagtgc cttcgacaag tttctcaatc actctgtgcc tcagcgtcct    300
cctctgtaaa acggcgaatg atggtagcgc ctacctcata agcttgtgag gattaagtga    360
gagtctatcc agtgttgagg agagtggcat aaataaagcg cctagtggta              410

<210> SEQ ID NO 2
<211> LENGTH: 542
<212> TYPE: DNA
<213> ORGANISM: homo sapiens

<400> SEQUENCE: 2
cctggaagcc cgctggtcac acaaaggaca aaggcatttc tatgttgggc ctcggtccct      60
tatcagtgca gctgaggaat gtctttagga caacccccctt tgctagtttt ccttctctgt   120
gcctgcagcc tgattttct ggctgtttct ctgtttaaag gagttttacc aaggacccgc    180
tctaactccc taaaggtttt tttctctcaa ggggacacac aaagttccaa tcacacacat    240
gcctccctat atccacttac cctctgcctc acagccaaat agatgctctg gtacggtcag    300
cgtctaaaga ttttacaaac aatatctctt cttctagttt gcagtcatta ttgaaataac    360
aaacatgtcc tattgtcagg ccttactctc agtaactgat ttcattgatc tgaataggaa    420
```

| | | | |
|---|---|---|---|
| acttacttga | ttaatcagct | actctttggt attacctgac atctcattaa tgcatctttg | 480 |
| aattgaatta | ttgctcaata | ggagtgattg tgaaatagtg gcaatgtatt acatcactat | 540 |
| tg | | | 542 |

<210> SEQ ID NO 3
<211> LENGTH: 1050
<212> TYPE: DNA
<213> ORGANISM: homo sapiens

<400> SEQUENCE: 3

| | | | |
|---|---|---|---|
| taataatgct | ggcttttggt | ttagtttcag taaaagaacc gggatggcaa aaggcttaca | 60 |
| gctggaagga | acttgctatg | agtcttagat gagactttgg acttttgttg ctggagcaag | 120 |
| ttaagactt | tgggactact | ggaatggaat gattgtattt tgtatatgag aagcacatga | 180 |
| ttttttgag | gctaggggca | gaatgctata tttgcatatg ttcatcacca tcaaaactca | 240 |
| tgttgaaatg | ttatttcag | tgccgcagta tagggaaatg gagcctaggg gagctgtttg | 300 |
| ggtcaaggga | atggatccat | tatgaatgac ttggtgctgt tctcgcagta gtgagctctt | 360 |
| gctctcatga | gactggatta | ttctcatgga aatggattag ttcccatgag agtgggttgt | 420 |
| tataaagcaa | gatgctcttg | ggttttgccc ctttgcacat gtctgcttcc cctttgacct | 480 |
| tctgccatgt | tatgatgcag | cacaaaagcc ctcaccagaa gccaagctga tgctggcacc | 540 |
| gtgcttcttg | tacttcccag | cctgcagaac catgagctaa ataaaccttt cttataaatt | 600 |
| atccagtctg | atgtattatg | ctatagcaac acaaaataga ctaagacggg tgttattatc | 660 |
| caaattaatt | tattaggcag | aacacaatca catgatttat acaaaggaat tagcagagaa | 720 |
| gacacagttt | tcggtactac | cgttgaaaaa tttgttcctc agagttggag tgtgctgtgg | 780 |
| gatacactaa | tggggatgtt | acacagatta ttttagcatg ttttactgct ttcacttcta | 840 |
| agaggtaagc | gacattgaag | tatcatgtct ttcctccaga ctggaacctt tcatggtcag | 900 |
| agatatcctg | ttaatgcctg | ttttttatttc tgcaataaag ccatgaaagt aataaattgg | 960 |
| atgggaagga | tctttgaggc | caatggtcaa aatataagat ttccaaaaga aaaatgtcat | 1020 |
| cagcctgtag | gaacacatgt | tctggcttgc | 1050 |

<210> SEQ ID NO 4
<211> LENGTH: 1359
<212> TYPE: DNA
<213> ORGANISM: homo sapiens

<400> SEQUENCE: 4

| | | | |
|---|---|---|---|
| aaaacatttg | ctgactgctg | ttctatctag gatatcatca gtgtgtagat gatcagagtt | 60 |
| catgtcagtg | ttcctacaag | ccaatgaaga aaaacagaga tctgtgttct gaatggaaaa | 120 |
| attcctactg | atgccagtaa | gtgagccatc catctatgat gtgtctatgg ggaagaaagt | 180 |
| gacatgaatg | agtaaaatag | aatatatgct ttaaatcatg aaaattgagt ccagatggaa | 240 |
| aggttaggag | gaaatggagt | ggaaaggtgg atgaagaaga gtgagaactc atgcagtcgt | 300 |
| tgcgacttgg | ttgacacttc | cttccctgtg actacaattc caagttcagt actcctgagc | 360 |
| ttttatagat | ggatgagaat | ataggggaa gaaacaagag gaaggagttt tctgaaatct | 420 |
| cggtggagag | gagggagaaa | aaagatggga aaatgttaca agcattctgt tcatgttgta | 480 |
| tcacttagtg | cagtcttgtc | ttcccagccc actagtctgg aacaagtcag tctcaaacat | 540 |
| aacaacagac | actggggagc | tctccaacaa aagatcacct cccaaagaac aggatggtgt | 600 |

| | |
|---|---|
| cgaagactga atgccagcct gaggaaacag aaatactaca gaagcacgcc agagcctgca | 660 |
| gtgtctcctc gctgcctctc aatgaactgc taaaagacca agaactctgc tgagagataa | 720 |
| gaagagggga gggtgtgctg caggtggtgc tgggaggccc agaccttctc ctgacatctg | 780 |
| gggctggcta caggaaacag aaacatcacc caggccttgg cgcgagacag gacagaggca | 840 |
| gattgtgact cagatctgca ggtggaaagt gggccttttcg ttttctccta ggggtagagc | 900 |
| aaagccagag ggctcagtca gaggaaacct aaggcagttc atgatccctt caactttata | 960 |
| ccatttcctc aaaactgcct ccaaacagtg ggcaactgga aaggtggtct gacctccagt | 1020 |
| gatcacacag tatgcattat aacagaaggc tgtcactgtc aattgcatgg ctccctcact | 1080 |
| atgcattcct tctatcaatt tacgacaaca cactgtagtg agtacctgca cattgctggg | 1140 |
| tattttggca gacattgata gtagatgaat aacacctggt acttgacctt gagacgctca | 1200 |
| ctgcctagtg tggggaacca atggttgcaa tataaagtat taactagagg gatagaggac | 1260 |
| tgcctgagga tctctgcact cagaggaagg gccatgagat cagccaggac agtagggagg | 1320 |
| cagtgactca tgaaattagc aagtggtgag aagagggca | 1359 |

<210> SEQ ID NO 5
<211> LENGTH: 2383
<212> TYPE: DNA
<213> ORGANISM: homo sapiens

<400> SEQUENCE: 5

| | |
|---|---|
| caagcataca cattttata accaaattag gaatattgat tttaaaaatc ttcaaatttc | 60 |
| cttacaatat atagtaggtg tccccaaccc ctgggccaca gactggtacc acgctgcaga | 120 |
| ctggtagctt tctgtggcct gttaggaagt gggctgcaca gcaggaggtg agttgcagtt | 180 |
| taactagcat taccgcctga gctccgcctc cggtcagatc agctgggcat tagattctca | 240 |
| caggagcaag aatcctattg gaactgtgc gtgagaggca tctaggttgc actctcctta | 300 |
| tcagaatcta actaatgcct gatgatctga ggtgaaatag tttcatcccg aaactacccc | 360 |
| cgactctgtc tgtggaaaaa ctatccccac aaaacctggt gccaaaaaga ttggggacca | 420 |
| ctgatatgta gggttccaat tattttggaa gacatgaatt aagagactgg ttgaagttca | 480 |
| ctaggcgttc tttgcttcta agtcctctgt cctctaggct gtgttgcata cataataatg | 540 |
| caagactgga ggacaccaat agcatctgca aatgacaaga taccttcaga tgaagcctaa | 600 |
| ttccaaaaag attaaatagt tatccacatg tagattatat aaactttag gaggttaatt | 660 |
| ctgtgggttg ctggattctg gctcccttat gccctgcaac cttatggctt catgctatat | 720 |
| atgaacttct tactaggaat aatggatgac ttgactgttc tctgcttcct gaacaacttc | 780 |
| taccatcatg ttaaattgaa gcttctcagt tatgccaagt tattcaatat atgatgtcct | 840 |
| atgttcctca tctttgcact ggaaataatg ctgtcaactc aaatgcttga tcaaaagtat | 900 |
| tgattatctg gtgtcagctg ttttcctgaa ttcatgcagt actgacaaag aagaatttgg | 960 |
| aattaaatac cagagaagag ttctattcca cctagagggt acagttttgt gacaatattt | 1020 |
| ttgacattct aattaggtta tcagcctatg attgcaaata aaaaatgaaa caataataat | 1080 |
| atttaaatac aaaggtattt aaagtaatga agcaaaagt ctaatgtaca tctttagttc | 1140 |
| ttttttcata gctgagttaa taaatacttt ttgtatcaag ttaatttgat ataaaaagta | 1200 |
| attcttatat attactaatc aagataatat gaattacaac aaagcattac ttagaaatat | 1260 |
| aatattaaaa tgcaacagct ttaaatccta ttgcccaat ggatattacc tacaagtcag | 1320 |
| gctctgtaca aacccattca gaatgctcca gctgacagtg cagtatttta tgccaatcaa | 1380 |

```
attatgttat tgtgatagaa catgatatgg attttaaga aaaaaatgat ccaatacaaa      1440
actgttatat acttggccct catccccatg atcacaaatc ccagaatttc aagaaaattt      1500
ggccaactga agtaaattgt aaattgtgtt tacactgtca cataggtggc atcactatag      1560
ctaagacaca aagtattctc tgtgtattgt caagattatc ctgaaatacc ataatttta       1620 aaagttttca ggacatatct atttatctaa tgttatatat atttaaataa aatatctata      1680
ctattttaat atataccttta attttctctg ctatgtgttt aattctgtca tgtaaaaaag     1740
agacacgaaa attgtaaccc ccagcacctt agaatgtgaa cttatttgaa atggaatca       1800 tcacagaggt aatctggttg aaatgagctc attaggatag acggtaatcc aatatgactg      1860
ggctacttat agaaaagaga aaatttggac acagatagac acatagaggg aagatgatga      1920
agatacacag agagaatgcc actgaagatg gaggtagaga ttgcaattat gttgccacaa      1980
accaaggaac atctgggatt gccagaagca ggaagaggca aagaagtaac cttctctaca      2040
ggtgttagag ggagcatggc ccatcaatcc cttgatttca cacttctagc ctttagaact      2100
atgaaacaaa acttttccct tgttctaaga catctaatgt ataatacttt gctattgcag      2160
ccataggaag ctataccttc tttccttcac tattaaaaat tttattgttc tctttcaact      2220
cctttgacat catgtctatt cctttataac taaagtcaat gattaattaa agaataatat      2280
ctctttctaa gtgtaaggtt gtgttccaac tgtcttacat acattaattc atttaattct      2340
tacaacaacc ctgtgaagta aatactatta ttttgctttt tac                       2383

<210> SEQ ID NO 6
<211> LENGTH: 298
<212> TYPE: DNA
<213> ORGANISM: homo sapiens

<400> SEQUENCE: 6
ctccctgcag cattttaga aggtaccaaa taagaaaaac gtggatgaag atggagaaag       60
catacaaaac ttttacacac tggtttgaag ggcaagccgt tgtacattcc ttgaagtcag      120
gtgctctgct caacagaagg tgtgctgaat aacgttacag gctctgttcc cgggagacgt      180
ggaagctgtc accgcgcgga acataaagaa caggccaaga ccagtgcagg catcgacgac      240
tttctccatt cagagcctcc gcgcatccca aataaataaa cacatcaaaa cgtgcaaa       298

<210> SEQ ID NO 7
<211> LENGTH: 757
<212> TYPE: DNA
<213> ORGANISM: homo sapiens

<400> SEQUENCE: 7
ggtgacactg gattctctcc atcatggagg gggtgggcct ttgcttggga aaacacaggc      60
tttctgcatg tgggttttcc tctctatgat cgtgcttttg ccggcactat tatcccaaca     120
ttgcctctga ttaatgtgct tattgcacag aggacatgcg ttgaaggact caggcccaga    180
ggactcacca tactacacct agcttccctc tcacccagaa gcagctaacc tgatgaaaca     240
aatgccctgg ccttgggaag acttagctat atcctaattg gagccaacac ccagaaaaaa    300
agaagcactg tcctaaagat agtagatgat ttgaatcagc gtgtgatatg gggtgctgat     360
ttttccaaag cttgaatata tgggtccagg aatcaaggac caagtgggag tgttttctcc     420
actattacac aagatttctc acttacagaa ttttatatt cttcctctat caagctctac      480
tacctttggt tccaacggaa acatgcctgt accagggcca gcaccctcga acagtgactg    540
```

| | | |
|---|---|---|
| acaggagctg gtatttatat attccagatt cttctttggc tggagacaac cctgaggtgt | 600 | |
| gtgtttcatg ctatctgaaa cccccgtggg attaaactcc tgttgcatgt agtggtaacg | 660 | |
| agtttgataa cacattctgc ctacattttt ttaatcttat ttcctcctcc tctactggtg | 720 | |
| gttcctgaaa ctcttaaata aattgattag actcaaa | 757 | |

<210> SEQ ID NO 8
<211> LENGTH: 1096
<212> TYPE: DNA
<213> ORGANISM: homo sapiens

<400> SEQUENCE: 8

| | |
|---|---|
| tagcaactcc acatttttt attcactcac aaagacacat ggtcataaat aaaatgcatg | 60 |
| gaaccagcga gacaatagca cagcagtaat gtcattttat atgcagcatg gccctgttgt | 120 |
| gaacggaatg attgtgaacg gaatgatggc caaggagctt tatgcttctg caccgccagc | 180 |
| tcacacgatg gtccgtgtat tgccccgtgg aaaaccgggg gtggaaagct gtctccacgt | 240 |
| tctgctgccg aagcagcaag ctgattcaca catcttgaag gcacagtgga acatggaagg | 300 |
| gtgcatatga acttgatttt tgaggatgaa acttcctgtc tgaatcgcta agtctcccag | 360 |
| cagggggtgtt aatgtccctg tgagatgcag gcttcccaca gacacaccca ggttgcgagt | 420 |
| gggttcaaca tggtcacagg agcttcaaat ggtaagatgg caagatctgg tagcatactg | 480 |
| agaccaccaa ccaggaatgg aggcttgctc ccaagtaact aaacatggac ttgtctctga | 540 |
| cacggaaaca atgtgaaaca cagaaggctt ttgagactca gaggcactcc aacaatgata | 600 |
| cttgaaaacc agaacagagt ttgacacaga tggatgcttt ccaaatgtca tgtcattttt | 660 |
| tcatatgtca agggcgaccc aatgtttgct tcctgttccc taggtgggtt ttccatgggg | 720 |
| actgcttcta accccaatc cccacacact ccacctgggc tgaaactgct gcctcttttc | 780 |
| caatatatag aaagaaatgt ggctccaccc tgcatttccg taagactcag ctagttacaa | 840 |
| atttagaacc ttggaaacaa tgataaaaca ttcttcaaga gaaataatc tccaggtttt | 900 |
| gtttcattat ctgtgagact attcagtgct acatctgctg aagggcataa aatccatatt | 960 |
| tttgttttaa aaatgggtct actttgatgc agcacccaaa tttaattact cttaaagctt | 1020 |
| tttaggatcc cagatgaaag atgctactgc agtgtaaagt tctaatatta tttatttccc | 1080 |
| tagtcatcaa cattag | 1096 |

<210> SEQ ID NO 9
<211> LENGTH: 1589
<212> TYPE: DNA
<213> ORGANISM: homo sapiens

<400> SEQUENCE: 9

| | |
|---|---|
| tagtatgttt ctatccacctt aatgaggccg cagatggagt cagaatgtga aattacaaat | 60 |
| aatcactgga tccatctact gttttccatc accttcccca ctgatgctct gggcgagaga | 120 |
| gtgatgtgtc acttcaactg tgtgtaatat gtcagacacg tcctacaata acaggcgtca | 180 |
| tatttgtatt attttagtt tactgtagaa ataatgtca ccgccaaagg tgatgagagt | 240 |
| cacgttttgt aggatctgtt ttcttatact taaagacaga cttctgctac ggtaattgcc | 300 |
| agtattcatg gcttcctttc tgtgtcagaa gagaagggat ctgctttctc ttggctgatt | 360 |
| tcacatagca ttggtaatag acatgcattt ctctttctaa agggagtaa cttttttaaac | 420 |
| ccttcctgat tttagcctgg caatgtaagt gtccttaatg tgactgtttt gataattaaa | 480 |
| aaaaggtata aatttattt aaatcttcat ttccttctt ttcagaaggt ccccaaatca | 540 |

```
cagttaactc attcattgac gcattcactc aacaactatt caatgaggca ctctctagag      600
accaaggata aataaggtag ccagtctcat agagatatga ggagatggaa attaatcaaa      660
taattcaagc aaatggcatc ttgcaacttg tgctgagtat aatggtgaaa aggcaaatga      720
tggcatgaga gcttatagta gggaaatttg gcctatttgg ggagatcagc ctacctgagg      780
aaggaatgtt ttagctaaaa tctgaaggat gagtattact taactagtga atgcgggagg      840
aaagagcatt ctaggcagag aacagtatgt gcaaaggtcc tggggcagga aaagcagagc      900
aggtttatag aacttaaagg agaactgtat gactgtgcca taaaaagtac agagaagtaa      960
ggcatgagtt acggttggac aagcaggcag gggctaggct gcctggagcc tgtgggccat     1020
ggtagagttt gtctgtatcc taagacctaa gccacataag ggttctaagc aggaacctgg     1080
taagatcaca tttaatttta atttttttat tttatttttt attttgaga tggagtcttg      1140 ctttgttgcc caggctggag tgcagtggct caacctcagc tcactgcaac ctctgcctcc     1200
tgggttcaat caattctcct gcctcagcct cctgagtagc caggattaca tgtgtgccac     1260
catcacgcct ggctaatttt tgtattttta gtagagacgg agtttctcca tgttggtcaa     1320
actggtgccg aatgcctgac ctcaagtgat tcaccagcct cggcctccca aagtgctggg     1380
attacaggag tacgccacag cgcccagcca ccaaattaat ttttaaagat cactatgatc     1440
gctgtgtgga aaatgagctg ggagtggtgg tggatacagt ttttgttttt gtttcagtct     1500
ttccctactc catgaaacat ttgcgctata tatgcggcca aatggaatgt ttctcttttc     1560 tccctcctc ttcctcttgg gaagtcacc                                         1589

<210> SEQ ID NO 10
<211> LENGTH: 520
<212> TYPE: DNA
<213> ORGANISM: homo sapiens

<400> SEQUENCE: 10
cctgcccact gggtgaaact gcaagtcgag agcgtgggaa accagcaagt tgagagagga       60
tccagaagta acccccttcta aaacgggaaa gatgccttcc gaaagaccgg atggcctggt     120
actggtcttc tctagactga aggtcctcca ccaggtctcc tgctgctgct acctaagaaa      180
gaaatctcac aagggtgtta aaagcacttg gccctaaaga gaaaacacta ggaggatggg      240
aaccagggac agagaagcta cttgctctgc agctgtttgg gccaatgatc caatggcccc      300
atctagactg gagacaccaa ctcatgactc agctggcctt gtggcccaca cccagaagtg      360
gactcagtgc atgaggacta ttttccacac tcctatgata gcatccccaa ccaatcagca      420
ggaccatttc ctagccccctt gcccaccaaa ctatctttta aaaaccctgg ctgggcgcag     480
tggctcacac ctgcaatccc agcactttgg gagtctgagg                            520

<210> SEQ ID NO 11
<211> LENGTH: 810
<212> TYPE: DNA
<213> ORGANISM: homo sapiens

<400> SEQUENCE: 11
aggcaacaga tgactttctg caaaggcact gataatagct atgaggaata aatattgcag       60
atggattaaa tcaaagaatc aaatttcaaa gccaaattag tcgtgaaaag gagggagaag      120
cagaaatgaa gaaaaaagaa ccacagaagt aaaatcagca gcattgaaaa gaaaatcatc      180
tgctgtttga ataaagaccc aagatctttc attgttggat ccccaaagcc agtgcctttt      240
```

```
ttgagcagca agtcccaaga tcaagaaatc agaaggaact aatactttaa ctaattagta    300
gtaatgaaaa tttactagac atcaatgaca aatttacaag gcaaatttat ttccaaagta    360
cattcatata tatcacagga tcacttcact gaggaactga acacgagcat ttaacttgtg    420
tgactagtta tggcctggtc tggatttcct tctggttctc aagatgtctt acatgaaaaa    480
agctctgtgg cacattacat tgggagctg ctgattaaag acatataagc tcttttgctg    540 accattttc cagaaccttg actgaatgt taatatccat tgtaaatctc taagtgggta    600
ccagtgttct gcaaagcact ctgggaaatg tttcccttc ctttatcttt tttagccagt    660
cccaatgtat tataacttga gtgaaacaga gctgtcctat acgccactct cagcatactg    720
agacatccaa aggaaatcca agtctggctg aaaaaatcac ccaccttgaa aaacaacgta    780
tgttgatcaa gacagatgcc tcttggagag                                    810
```

<210> SEQ ID NO 12
<211> LENGTH: 1755
<212> TYPE: DNA
<213> ORGANISM: homo sapiens

<400> SEQUENCE: 12

```
gtggaattat aaaacctttg gaaaatcttt catgtgagaa caacatgggg gcaagcctct     60
gaccaaaata gctcaaaaat ttgtgttacg cagttacagt aaatacccaa gagcttgacg    120
cataaaacac aacagcctcc tggagacaga gggaggagaa agaaagataa agtctgtggc    180
tttagaagaa aaggaataac ttaagaggct tgtttgctgt tcaggctggc caccaaggat    240
gacattttgg atactataag aagattggga tagatactga gtgagcctca gaaaatcagc    300
tggatacacc ccagctccct cccaccacat gaactaaaga tctgcaagct gtaaccttt    360 ccgaagggct acctgggcct ctgtgtccat cagagctgat gagctgatct tcattcacca    420
taagtgcaac tatcatggct catggagccc tggagagagt agcacatata ttgaacttca    480
gttttaaaaa gtctaatact tttctaaaat gacttgctat ctatttcatc cagagaagat    540
ttattacgta gcctttctag cataaaatat cattactttt aaagaaaaat ccaatctaaa    600
ttcctctaac tacaatggaa gtccccttt cttattcatt tctcactcaa atatggaaca    660
accagtcact tccattaaat ctaatcttcc tgtatgctct tgaagataac taccagttaa    720
acagagctat ctatgggaat ggttttgaa aaaaaattgc gttgtttcag tactttggag    780
gatggctgat gtttgccttt tcaagagatg tatcatggac tgttttttgtt aaactaactt    840 ggcttcaaga atttgagact aactcagatt ttctcaaaca gtgggggatt tgatgcagca    900
atatgcaggc atgggatatc agaaagagcc agataaccaa aggaagagta gtagctgaag    960
caggattcta agaccaagaa atcattttca tgctgcatta cggttgccag attagtcatt   1020
aaataaacag tatacaattc attgaactct ctgttagccc atttgaaaga tgatgaagtt   1080
agaatgctta atatatggtc ctttgtgttt ggagcagata aaagcgttct ggaaaattcc   1140
caagagtaga atattaattt cagggcagaa agatttttg ctgtttcggt cgtggcatta   1200
tctccagtat ttatgtgcct ggaacatatt agttgcccat gctttgacga gtgggatggc   1260
cctttgaagc agagacacac ctttctcct gggtgctacc tgagcacttc ttacaaaacc   1320
atttgtttta ttatgacatt tagcagattg tgttattttt actcacatgc caaatgctgt   1380
acttcaatat gagcttttca agaagtaaag aatagtgaat tattcctatt tgtaacacag   1440
atatgagcca ccaggggcaa ctatatgcaa actaaattga tagctatgag gtcatagtgt   1500
tgaactgttg ttgcgaatac ttctctcgta gacaccctga gaagtgatag tgagttcatg   1560
```

| | | | |
|---|---|---|---|
| ctaaagctac | agtctaactt | tctaaaaaga gttgaaatta tctcatattt aacattctgt | 1620 |
| gaattccatg | tccagaagag | ttcagggtta tcaatgcggt attttctcaa aatagaacca | 1680 |
| ctctgttctc | caaggactta | aaatatagaa gcccaggaaa tattctgtca gttattaaaa | 1740 |
| atgtccacta | acaca | | 1755 |

<210> SEQ ID NO 13
<211> LENGTH: 430
<212> TYPE: DNA
<213> ORGANISM: homo sapiens

<400> SEQUENCE: 13

| | | | |
|---|---|---|---|
| ggacatggaa | atttctagaa | agaaggcgca agcaggacac cggcgataaa aagttccctt | 60 |
| tgtaaccaga | ccagctgaga | ccagttacaa agcctacccc aggtatccga ccagatgact | 120 |
| tcaaaaagac | ctcaggcttc | attataatct aatttccatg ctaaatgaca cttccaccag | 180 |
| tgtcatgacg | gttgccagtc | cccgtgacaa tgaccagaag gagccataaa aggacaaaaa | 240 |
| caagggagcc | cctcattcca | agaagtgtac cgcccagttc cagaaaagac atggatattc | 300 |
| ctcctcttgc | ttttaatgtc | cagccatcat taaggaaacc ctatatgata accccctcac | 360 |
| ccctcactaa | ttgagaagtt | gatttgtgag ccaagctccc gcttctcaat tccatggcca | 420 |
| tcgaataaag | | | 430 |

<210> SEQ ID NO 14
<211> LENGTH: 406
<212> TYPE: DNA
<213> ORGANISM: homo sapiens

<400> SEQUENCE: 14

| | | | |
|---|---|---|---|
| cacatccagt | acatgaataa | atgaaaaacg caagttacaa aacattacag aggtaaaatc | 60 |
| ataaatatag | tccctgaatt | tcatggccac ctgaccttca catgaagctc atattaaagc | 120 |
| catctataga | gcatgttttc | ctgaaaactt gacaagtgag tacacacaac ctctctttct | 180 |
| ttggtcatgt | ggagatagga | gttttgtacc ataaaaggca tagcccaaag tgtcaattgt | 240 |
| ttagctccct | aagaggcagg | cccatggtcg tcttaaatgc cagcagcagg ttgaagtcac | 300 |
| ctggaatggt | gtttcagaga | aatcctcttt agtataggga aggcttgtag tctgagaaat | 360 |
| cattccatgt | tggaattggg | aataaagaca gtcctctcac catcct | 406 |

<210> SEQ ID NO 15
<211> LENGTH: 600
<212> TYPE: DNA
<213> ORGANISM: homo sapiens

<400> SEQUENCE: 15

| | | | |
|---|---|---|---|
| tgttcaggct | ggccaccaag | gatgacattt tgctgcagca gagccatcag aaaacaactc | 60 |
| ctgattttag | ttgatcagat | tcaagtcaat gaaaaaatga cgtttctgtg tgtctacttc | 120 |
| gggctaagca | ccagggtagg | cacaagagag atcacaggga tgaattagtc ctagccccctt | 180 |
| ggagattatc | ctctcaccct | ctccccgcca tagttatctt ggtccttttc acatatatct | 240 |
| tagcaggttc | tgtttcaggc | aaagtttcac ttctgtatat gtttgttact actgttcatt | 300 |
| tgagatctgc | cactaaccct | cattatgacc tgggacatgt ctgtggcccc tccacatgct | 360 |
| ggcaggataa | aaattgacca | aatatatgat gctgtcacat agatggatcc tattatttgg | 420 |
| tgattacatt | gaaatcttta | ctgtaaaaat tgtgttgtca aaaatgaaaa cagatgatac | 480 |

| tgagtaactc actagtgccc taaagtactc tacagctttt caaacaaaat tgaatattct | 540 |
| tttcaacatt ctctctgtaa aaaaaaaaaa caattctata ttagtgaccc tatatccaat | 600 |

<210> SEQ ID NO 16
<211> LENGTH: 581
<212> TYPE: DNA
<213> ORGANISM: homo sapiens

<400> SEQUENCE: 16

| gataaatttg cacagggaca gatgctcagg ggaaaggaaa gagctctgcc ttgcacttgt | 60 |
| acagaaagga acaaggcag cagaggcaag accaatggag agtacggcag caagacagaa | 120 |
| aggggcagaa ggcgacagaa catgcacgct ggggacatgg aaatttctag aaagaaggcg | 180 |
| caagcagaaa caggacaccg gcgataaaaa gttccctttg taaccagacc agctgagacc | 240 |
| agttacaaag cctaccccag gtatccgacc agatgacttc aaaaagacct caggcttcat | 300 |
| tataatctaa tttccatgct aaatgacact tccaccagtg tcatgacggt tgccagtccc | 360 |
| cgtgacaatg accagaagga gccataaaag dacaaaaaca agggagcccc tcattccaag | 420 |
| aagtgtaccg cccagttcca gaaaagacat ggatattcct cctcttgctt ttaatgtcca | 480 |
| gccatcatta aggaaaccct atatgataac cccctcaccc ctcactaatt gagaagttga | 540 |
| tttgtgagcc aagctcccgc ttctcaattc catggccatc g | 581 |

<210> SEQ ID NO 17
<211> LENGTH: 1480
<212> TYPE: DNA
<213> ORGANISM: homo sapiens

<400> SEQUENCE: 17

| aggcgcaggc gcggaggggc gcgcccgaac ccgaacccta atgccgtcat aagagcccta | 60 |
| gggagaccttt agggaacaag cattaaactg acactcgatt ctgtagccgg ctctgccaag | 120 |
| agacatggcg ttgcggtgat atgagggcag gggtcatgga agaaagcctt ctggttttag | 180 |
| acccacagga agatctgtga cgcgctcttg ggtagagcac acgttgctgg gcgtgcgctt | 240 |
| gaaaagagcc taagaagagg gggcgtctgg aaggaaccgc aacgccaagg gagggtgtcc | 300 |
| agccttcccg cttcaacacc tggacacatt ctggaaagtt tcctaagaaa gccagaaaaa | 360 |
| taatttaaaa aaaaatccag aggccagacg ggctaatggg gctttactgc gactatctgg | 420 |
| cttaatcctc caaacaacct tgccatacca gcccatcagt cctctgagac aggcaagccc | 480 |
| aagaaagtca ggggcctatg tgagccaaag aggagagaag gtgatgcctc agcccagtgt | 540 |
| ttctgcccca cctcgcttgt ggccttcgga acttgatttg caccgcagga aaatgggcaa | 600 |
| tgaaaacccc tccctaactg gcttctcagt ccactctgac cagcccactg cacagcgccc | 660 |
| accctgcagc tccagatgag gcctcactct gtcacccagg ttggggtgga gtggcacagt | 720 |
| cacagctcac tataacctca agctcctggg ctcaagtgat cctgccacct cagcctccta | 780 |
| agtagctgga actacagatg tgcactgcca tgccaggctt gtctaacatt tttatgtgtt | 840 |
| gcttcatcca gtttgctaga gtttttggag atttctgtct tcattcatga gggataatag | 900 |
| tctgcacttt tattttcttg tgatactttt gtctgatttg ttatctgggt aatactggcc | 960 |
| ttgaaaatga attgatgttt tcctgcttct ctgctttgca agtgtttgtg aaggattggt | 1020 |
| tattcattaa gtgtttaata gaattcacta gtgaagctat gtgagccagg gctagactga | 1080 |
| tgaagagttt tcattagtct aatctgttta cttgctgtat aagtacgcat atattctctt | 1140 |
| tcttcttgat ttaattttac actttgtgta tagcagggaa tctgtgtcta atttgtagta | 1200 |

```
tttcatgctt ctaggttttc atggcagttg agatgtaaga ataacaataa tgttgggaga    1260
aggaagttgt ggacaatcca tgaatatccc aacatctgtt gtaggaaggt taagattact    1320 ttttttttt ttgctgtact gaactgaata ctcttattta taatgtcaga caaatgtaat    1380
gttgtatata aatagaacta ggaaaatgtg ccatttgtct tagtatttaa tcaagatgga    1440
agtctgggcc tacctcctct cttttattaa tatgtagaca                          1480

<210> SEQ ID NO 18
<211> LENGTH: 22
<212> TYPE: RNA
<213> ORGANISM: homo sapiens

<400> SEQUENCE: 18
ugccuggaac auaguaggga cu                                                22

<210> SEQ ID NO 19
<211> LENGTH: 22
<212> TYPE: RNA
<213> ORGANISM: homo sapiens

<400> SEQUENCE: 19
auucuaauuu cuccacgucu uu                                                22

<210> SEQ ID NO 20
<211> LENGTH: 22
<212> TYPE: RNA
<213> ORGANISM: homo sapiens

<400> SEQUENCE: 20
aggaggaauu ggugcugguc uu                                                22

<210> SEQ ID NO 21
<211> LENGTH: 23
<212> TYPE: RNA
<213> ORGANISM: homo sapiens

<400> SEQUENCE: 21
ugagcgccuc gacgacagag ccg                                               23

<210> SEQ ID NO 22
<211> LENGTH: 22
<212> TYPE: RNA
<213> ORGANISM: homo sapiens

<400> SEQUENCE: 22
ugagggagua ggauguaugg uu                                                22
```

EXOSOME PROFILING FOR DIAGNOSIS AND MONITORING OF VASCULITIS AND VASCULOPATHIES INCLUDING KAWASAKI DISEASE

INCORPORATION BY REFERENCE TO ANY PRIORITY APPLICATIONS

This application is a U.S. National Phase Application of PCT International Application Number PCT/IB2018/056292, filed on Aug. 20, 2018, designating the United States of America and published in the English language, which is an International Application of and claims the benefit of priority to U.S. Provisional Application No. 62/548,330, filed on Aug. 21, 2017. The disclosures of the above-referenced applications are hereby expressly incorporated by reference in their entireties.

STATEMENT REGARDING FEDERALLY SPONSORED R&D

This invention was made with government support under R01 FD003526 awarded by the Food and Drug Administration. The government has certain rights in the invention.

REFERENCE TO SEQUENCE LISTING

The present application is being filed along with a Sequence Listing in electronic format. The Sequence Listing is provided as a file entitled SeqList-SCRI-097NP.txt, created Feb. 18, 2020 which is about 22 kb in size. The information is the electronic format of the Sequence Listing is incorporated herein by reference in its entirety

FIELD OF THE INVENTION

Some embodiments of the methods and compositions provided herein relate to the detection of biomarkers for Kawasaki disease (KD), the diagnosis of KD in a subject, and/or the amelioration or treatment of KD in a subject. In some embodiments, a biomarker can include a long intergenic non-coding RNA (lincRNA). In some embodiments, the biomarker is present in an exosome-enriched serum sample from a subject.

BACKGROUND OF THE INVENTION

Kawasaki Disease (KD) or Syndrome is the leading cause of acquired heart disease in children the United States. The Center for Disease Control estimates that over 4000 U.S. children per year are diagnosed with KD. Although, KD qualifies for Orphan Disease status by NIH and FDA standards, it is a growing and important health problem for children in the U.S. and worldwide. KD is an autoimmune disease and includes vasculitis with a specific predilection for coronary arteries, causing aneurysm and/or ectasia. Although, the majority of patients do well, many experience long term coronary artery abnormalities.

Vasculopathies, such as Kawasaki disease (KD), attack the coronary arteries of disease sufferers, which can result in debilitating coronary artery aneurysms followed by thrombosis, stenosis, and even myocardial infarction and death. However, if vasculopathies, such as KD, are diagnosed and treated early, the associated health complications and mortality rate are minimal. KD is most commonly treated with intravenous gamma globulin (IVIG), which is most effective if initiated within the first 10 days of fever onset.

KD is often misdiagnosed or diagnosed too late for therapy to prevent the onset of coronary artery disease. This occurs because the hallmark clinical feature of KD is persistent fever, and then a clinical diagnosis is usually made by the presence of various clinical criteria, including rash, swollen lymph nodes, swelling of hands and oral changes all symptoms that are present individually in other childhood diseases. Further, children with KD frequently have preceding viral infections and then show positive markers for those viruses, which can further cloud the diagnosis of KD. Identification of a specific biomarker for KD would facilitate a more timely, and accurate diagnosis of KD, and would allow for therapies to be administered within the time frame to see clinical improvement.

SUMMARY OF THE INVENTION

Some embodiments of the methods and compositions provided herein include a method of detecting a Kawasaki disease (KD) biomarker in a subject comprising: detecting the presence or absence of a KD biomarker in a biological sample from the subject, such as a serum sample, wherein the KD biomarker comprises a long intergenic non-coding RNA (lincRNA).

In some embodiments, the biological sample is enriched for exosomes. In some embodiments, the biological sample is enriched for CD31+ exosomes.

In some embodiments, the lincRNA comprises at least one of linc-MBOAT7, linc-ZNF337-1, linc-RBM45-2, linc-WDR7-5, linc-CISD1, linc-ADARB2-2, linc-COBL-2, linc-NPVF-2, linc-P2RX4, linc-CXorf36-3, linc-CD180-9:copy2, linc-ELMOD1, linc-LAMA1-1, and/or linc-NUDCD2-3. In some embodiments, the lincRNA comprises at least one of linc-MBOAT7, and/or linc-ZNF337-1. In some embodiments, the lincRNA is comprises at least two of linc-MBOAT7, linc-ZNF337-1, linc-RBM45-2, linc-WDR7-5, linc-CISD1, linc-ADARB2-2, linc-COBL-2, linc-NPVF-2, linc-P2RX4, linc-CXorf36-3, linc-CD180-9:copy2, linc-ELMOD1, linc-LAMA1-1, and/or linc-NUDCD2-3. In some embodiments, the lincRNA is comprises at least three of linc-MBOAT7, linc-ZNF337-1, linc-RBM45-2, linc-WDR7-5, linc-CISD1, linc-ADARB2-2, linc-COBL-2, linc-NPVF-2, linc-P2RX4, linc-CXorf36-3, linc-CD180-9:copy2, linc-ELMOD1, linc-LAMA1-1, and/or linc-NUDCD2-3. In some embodiments, the lincRNA is comprises at least four of linc-MBOAT7, linc-ZNF337-1, linc-RBM45-2, linc-WDR7-5, linc-CISD1, linc-ADARB2-2, linc-COBL-2, linc-NPVF-2, linc-P2RX4, linc-CXorf36-3, linc-CD180-9:copy2, linc-ELMOD1, linc-LAMA1-1, and/or linc-NUDCD2-3. In some embodiments, the presence of the lincRNA in the biological sample is indicative of the subject having KD.

Some embodiments also include detecting the presence or absence of an additional KD biomarker in the biological sample, wherein the additional KD biomarker comprises a microRNA. In some embodiments, the microRNA comprises at least one of hsa-miR-3116-1, hsa-miR-576-5p, hsa-miR-766, hsa-miR-339-3p, and/or hsa-miR-4510. In some embodiments, the presence of the microRNA in the sample is indicative of the subject having KD, wherein the microRNA comprises at least one of hsa-miR-3116-1, hsa-miR-576-5p, and/or hsa-miR-766. In some embodiments, the absence of the microRNA in the sample is indicative of the subject having KD, wherein the microRNA comprises at least one of hsa-miR-339-3p, and/or hsa-miR-4510.

Some embodiments also include contacting the biological sample with an anti-CD31 antibody or antigen binding fragment thereof. In some embodiments, the anti-CD31 antibody or antigen binding fragment thereof is attached to a substrate. In some embodiments, the substrate is selected from the group consisting of a bead, a membrane, a slide, a gel, and a microwell plate.

Some embodiments also include extracting RNA from the serum sample.

In some embodiments, detecting the presence or absence of a lincRNA in the biological sample comprises contacting a probe with a population of nucleic acids prepared from the biological sample, wherein the probe is configured to hybridize with a target nucleic acid having a sequence of any one of SEQ ID Nos: 1-14 or a complement thereof, or capable of hybridizing to a fragment of the target nucleic acid.

In some embodiments, the subject is human. In some embodiments, the subject is a pediatric subject. In some embodiments, the subject has symptoms of KD. In some embodiments, the subject has febrile symptoms.

Some embodiments of the methods and compositions provided herein include a method for diagnosing Kawasaki disease (KD) in a subject comprising: detecting the presence or absence of a KD biomarker in a biological sample from the subject, such as a serum sample, wherein the KD biomarker is a long intergenic non-coding RNA (lincRNA); and diagnosing the subject with KD when the presence of the KD biomarker is detected.

In some embodiments, the biological sample is enriched for exosomes. In some embodiments, the biological sample is enriched for CD31+ exosomes.

In some embodiments, the lincRNA comprises at least one of linc-MBOAT7, linc-ZNF337-1, linc-RBM45-2, linc-WDR7-5, linc-CISD1, linc-ADARB2-2, linc-COBL-2, linc-NPVF-2, linc-P2RX4, linc-CXorf36-3, linc-CD180-9: copy2, linc-ELMOD1, linc-LAMA1-1, and/or linc-NUDCD2-3. In some embodiments, the lincRNA comprises at least one of linc-MBOAT7, and/or linc-ZNF337-1. In some embodiments, the lincRNA is comprises at least two of linc-MBOAT7, linc-ZNF337-1, linc-RBM45-2, linc-WDR7-5, linc-CISD1, linc-ADARB2-2, linc-COBL-2, linc-NPVF-2, linc-P2RX4, linc-CXorf36-3, linc-CD180-9: copy2, linc-ELMOD1, linc-LAMA1-1, and/or linc-NUDCD2-3. In some embodiments, the lincRNA is comprises at least three of linc-MBOAT7, linc-ZNF337-1, linc-RBM45-2, linc-WDR7-5, linc-CISD1, linc-ADARB2-2, linc-COBL-2, linc-NPVF-2, linc-P2RX4, linc-CXorf36-3, linc-CD180-9:copy2, linc-ELMOD1, linc-LAMA1-1, and/or linc-NUDCD2-3. In some embodiments, the lincRNA is comprises at least four of linc-MBOAT7, linc-ZNF337-1, linc-RBM45-2, linc-WDR7-5, linc-CISD1, linc-ADARB2-2, linc-COBL-2, linc-NPVF-2, linc-P2RX4, linc-CXorf36-3, linc-CD180-9:copy2, linc-ELMOD1, linc-LAMA1-1, and/or linc-NUDCD2-3. In some embodiments, the presence of the lincRNA in the biological sample is indicative of the subject having KD.

Some embodiments also include detecting the presence or absence of an additional KD biomarker in the biological sample, wherein the additional KD biomarker comprises a microRNA. In some embodiments, the microRNA comprises at least one of hsa-miR-3116-1, hsa-miR-576-5p, hsa-miR-766, hsa-miR-339-3p, and/or hsa-miR-4510. In some embodiments, the presence of the microRNA in the sample is indicative of the subject having KD, wherein the microRNA comprises at least one of hsa-miR-3116-1, hsa-miR-576-5p, and/or hsa-miR-766. In some embodiments, the absence of the microRNA in the sample is indicative of the subject having KD, wherein the microRNA comprises at least one of hsa-miR-339-3p, and/or hsa-miR-4510.

Some embodiments also include contacting the biological sample with an anti-CD31 antibody or antigen binding fragment thereof. In some embodiments, the anti-CD31 antibody or antigen binding fragment thereof is attached to a substrate. In some embodiments, the substrate is selected from the group consisting of a bead, a membrane, a slide, a gel, and a microwell plate.

Some embodiments also include extracting RNA from the biological sample.

In some embodiments, detecting the presence or absence of a lincRNA in the biological sample comprises contacting a probe with a population of nucleic acids prepared from the biological sample, wherein the probe is configured to hybridize with a target nucleic acid having a sequence of any one of SEQ ID Nos: 1-14 or a complement thereof, or capable of hybridizing to a fragment of the target nucleic acid.

In some embodiments, the subject is human. In some embodiments, the subject is a pediatric subject. In some embodiments, the subject has symptoms of KD. In some embodiments, the subject has febrile symptoms.

Some embodiments of the methods and compositions provided herein include a method for treating or ameliorating Kawasaki disease (KD) in a subject comprising: detecting the presence or absence of a KD biomarker in a biological sample, such as a serum sample, from the subject, wherein the KD biomarker is a long intergenic non-coding RNA (lincRNA); diagnosing the subject with KD when the presence of the KD biomarker is detected in the serum sample; and administering a therapy for the KD to the diagnosed subject.

In some embodiments, the therapy comprises an effective amount of a composition selected from the group consisting of an intravenous immunoglobulin, aspirin, and a corticosteroid.

In some embodiments, the biological sample is enriched for exosomes. In some embodiments, the biological sample is enriched for CD31+ exosomes.

In some embodiments, the lincRNA comprises at least one of linc-MBOAT7, linc-ZNF337-1, linc-RBM45-2, linc-WDR7-5, linc-CISD1, linc-ADARB2-2, linc-COBL-2, linc-NPVF-2, linc-P2RX4, linc-CXorf36-3, linc-CD180-9: copy2, linc-ELMOD1, linc-LAMA1-1, and/or linc-NUDCD2-3. In some embodiments, the lincRNA comprises at least one of linc-MBOAT7, and/or linc-ZNF337-1. In some embodiments, the lincRNA is comprises at least two of linc-MBOAT7, linc-ZNF337-1, linc-RBM45-2, linc-WDR7-5, linc-CISD1, linc-ADARB2-2, linc-COBL-2, linc-NPVF-2, linc-P2RX4, linc-CXorf36-3, linc-CD180-9: copy2, linc-ELMOD1, linc-LAMA1-1, and/or linc-NUDCD2-3. In some embodiments, the lincRNA is comprises at least three of linc-MBOAT7, linc-ZNF337-1, linc-RBM45-2, linc-WDR7-5, linc-CISD1, linc-ADARB2-2, linc-COBL-2, linc-NPVF-2, linc-P2RX4, linc-CXorf36-3, linc-CD180-9:copy2, linc-ELMOD1, linc-LAMA1-1, and/or linc-NUDCD2-3. In some embodiments, the lincRNA is comprises at least four of linc-MBOAT7, linc-ZNF337-1, linc-RBM45-2, linc-WDR7-5, linc-CISD1, linc-ADARB2-2, linc-COBL-2, linc-NPVF-2, linc-P2RX4, linc-CXorf36-3, linc-CD180-9:copy2, linc-ELMOD1, linc-LAMA1-1, and/or linc-NUDCD2-3. In some embodiments, the presence of the lincRNA in the biological sample is indicative of the subject having KD.

Some embodiments also include detecting the presence or absence of an additional KD biomarker in the biological sample, wherein the additional KD biomarker comprises a microRNA. In some embodiments, the microRNA comprises at least one of hsa-miR-3116-1, hsa-miR-576-5p, hsa-miR-766, hsa-miR-339-3p, and/or hsa-miR-4510. In some embodiments, the presence of the microRNA in the sample is indicative of the subject having KD, wherein the microRNA comprises at least one of hsa-miR-3116-1, hsa-miR-576-5p, and/or hsa-miR-766. In some embodiments, the absence of the microRNA in the sample is indicative of the subject having KD, wherein the microRNA comprises at least one of hsa-miR-339-3p, and/or hsa-miR-4510.

Some embodiments also include contacting the serum sample with an anti-CD31 antibody or antigen binding fragment thereof. In some embodiments, the anti-CD31 antibody or antigen binding fragment thereof is attached to a substrate. In some embodiments, the substrate is selected from the group consisting of a bead, a membrane, a slide, a gel, and a microwell plate.

Some embodiments also include extracting RNA from the biological sample.

In some embodiments, detecting the presence or absence of a lincRNA in the biological sample comprises contacting a probe with a population of nucleic acids prepared from the serum sample, wherein the probe is configured to hybridize with a target nucleic acid having a sequence of any one of SEQ ID Nos: 1-14 or a complement thereof, or capable of hybridizing to a fragment of the target nucleic acid.

In some embodiments, the subject is human. In some embodiments, the subject is a pediatric subject. In some embodiments, the subject has symptoms of KD. In some embodiments, the subject has febrile symptoms.

Some embodiments of the methods and compositions provided herein include a kit for detecting Kawasaki disease (KD) in a subject comprising: a probe configured to detect the presence of a KD biomarker in a sample, wherein the KD biomarker comprises a long intergenic non-coding RNA (lincRNA). In some embodiments, the probe comprises a primer. In some embodiments, the primer is attached to a first substrate. In some embodiments, the first substrate is selected from the group consisting of a bead, a membrane, a slide, a flow cell, and a microwell plate In some embodiments, the lincRNA comprises at least one of linc-MBOAT7, linc-ZNF337-1, linc-RBM45-2, linc-WDR7-5, linc-CISD1, linc-ADARB2-2, linc-COBL-2, linc-NPVF-2, linc-P2RX4, linc-CXorf36-3, linc-CD180-9: copy2, linc-ELMOD1, linc-LAMA1-1, and/or linc-NUDCD2-3.

In some embodiments, the probe is configured to hybridize with a nucleic acid sequence of any one of SEQ ID NOs: 1-14 or a complement thereof.

Some embodiments also include an additional probe configured to detect the detect the presence of a KD biomarker comprising a microRNA. In some embodiments, the microRNA is selected from at least one of hsa-miR-3116-1, hsa-miR-576-5p, hsa-miR-766, hsa-miR-339-3p, and/or hsa-miR-4510.

Some embodiments also include an anti-CD31 antibody or fragment thereof. In some embodiments, the anti-CD31 antibody or fragment thereof is attached to a second substrate. In some embodiments, the second substrate is selected from the group consisting of a bead, a membrane, a slide, a gel, a flow cell, and a microwell plate.

Some embodiments of the methods and compositions provided herein include a method of treating, inhibiting, or ameliorating a vasculopathy in a subject in need thereof, the method comprising: obtaining a biological sample from the subject; isolating an exosome from the biological sample; extracting RNA from the exosome; analyzing the RNA extracted from the exosome for the presence of a marker for a vasculopathy, determining the presence of the vasculopathy based on the identification of the marker; and providing a therapy for the subject's vasculopathy. In some embodiments, the vasculopathy is vasculitis, atherosclerosis, inflammation within arteries, coronary artery vasculopathy after heart transplantation, and/or Kawasaki disease.

In some embodiments, the subject is of a pediatric age. In some embodiments, the subject is of an adult age. In some embodiments, the subject is febrile.

In some embodiments, the isolation of the exosome comprises selecting and/or isolating an exosome that comprises CD31.

Some embodiments also include preparing an RNA library from the RNA of the exosome.

In some embodiments, analyzing comprises identification of an RNA pattern of CD31+ positive exosomes.

In some embodiments, the therapy comprises administering intravenous gamma globulin to the subject.

In some embodiments, the RNA comprises mRNA, microRNAs and/or lincRNA.

In some embodiments, the RNA contents from an exosome of the subject comprises more lincRNA when compared to a control individual lacking symptoms of a vasculopathy.

Some embodiments of the methods and compositions provided herein include a method of treating, inhibiting, or ameliorating a vasculopathy in a subject in need thereof, the method comprising: obtaining a biological sample from the subject; isolating an exosome from the biological sample; determining the presence of CD31 on the exosome; identifying the presence of a vasculopathy in said subject based on the identification of CD31 on the exosome; and providing a therapy for the subject's vasculopathy. In some embodiments, the vasculopathy is vasculitis, atherosclerosis, inflammation within arteries, coronary artery vasculopathy after heart transplantation, and/or Kawasaki disease.

In some embodiments, the subject is of a pediatric age. In some embodiments, the subject is of an adult age. In some embodiments, the subject is febrile.

In some embodiments, the therapy comprises administering intravenous gamma globulin to the subject.

In some embodiments, the presence of CD31 on the exosome is determined by binding an antibody specific for CD31, a binding portion of an antibody specific for CD31 or a binding agent specific for CD31 to the CD31-containing exosome. In some embodiments, the exosome and/or the antibody, binding portion of an antibody, or a binding agent is/are attached to a solid support, such as a bead, membrane, lateral flow device or a microarray plate.

In some embodiments, the biological sample is whole blood, serum, plasma, urine, saliva, lymphatic fluid, or cerebrospinal fluid.

Some embodiments also include comparing CD31+ and CD31− exosomes for the presence or absence of specific RNAs.

In some embodiments, the RNA is a lincRNA. In some embodiments, the RNA is linc-ZAF337-1, linc-RMB45-2, lincWDR7-5, linc-CISD1, linc-ADARB2-2, linc-COBL-2, linc-NPVF-2, linc-P2RX4, linc-CXoff36-3, linc-CD180-9, linc-ELMOD1, linc-LAMA1-1, and/or linc-NUDCD2-3.

Some embodiments of the methods and compositions provided herein include a method for identifying a biomarker of Kawasaki disease (KD), comprising obtaining a test sample, such as a serum sample, from a subject having KD, and a control sample, such as a control serum sample, from a subject not having KD; enriching the test sample and the control sample for exosomes comprising a marker for an endothelial cell; identifying differences between the test sample and the control sample, thereby identifying a biomarker for a subject having KD or not having KD. In some embodiments, the marker for an endothelial cell is selected from at least one of CD31, CD105, and CD146. In some embodiments, the marker for an endothelial cell comprises CD31. In some embodiments, the enriching comprises contacting exosomes of each sample with an antibody or antigen binding fragment thereof which specifically binds to the marker for an endothelial cell. In some embodiments, the identified marker is selected from the group consisting of a polypeptide, and a nucleic acid, such as an RNA or DNA. In some embodiments, the identified marker is a polypeptide. In some embodiments, the identified marker is a long intergenic non-coding RNA (linRNA).

DETAILED DESCRIPTION

Figure 1:
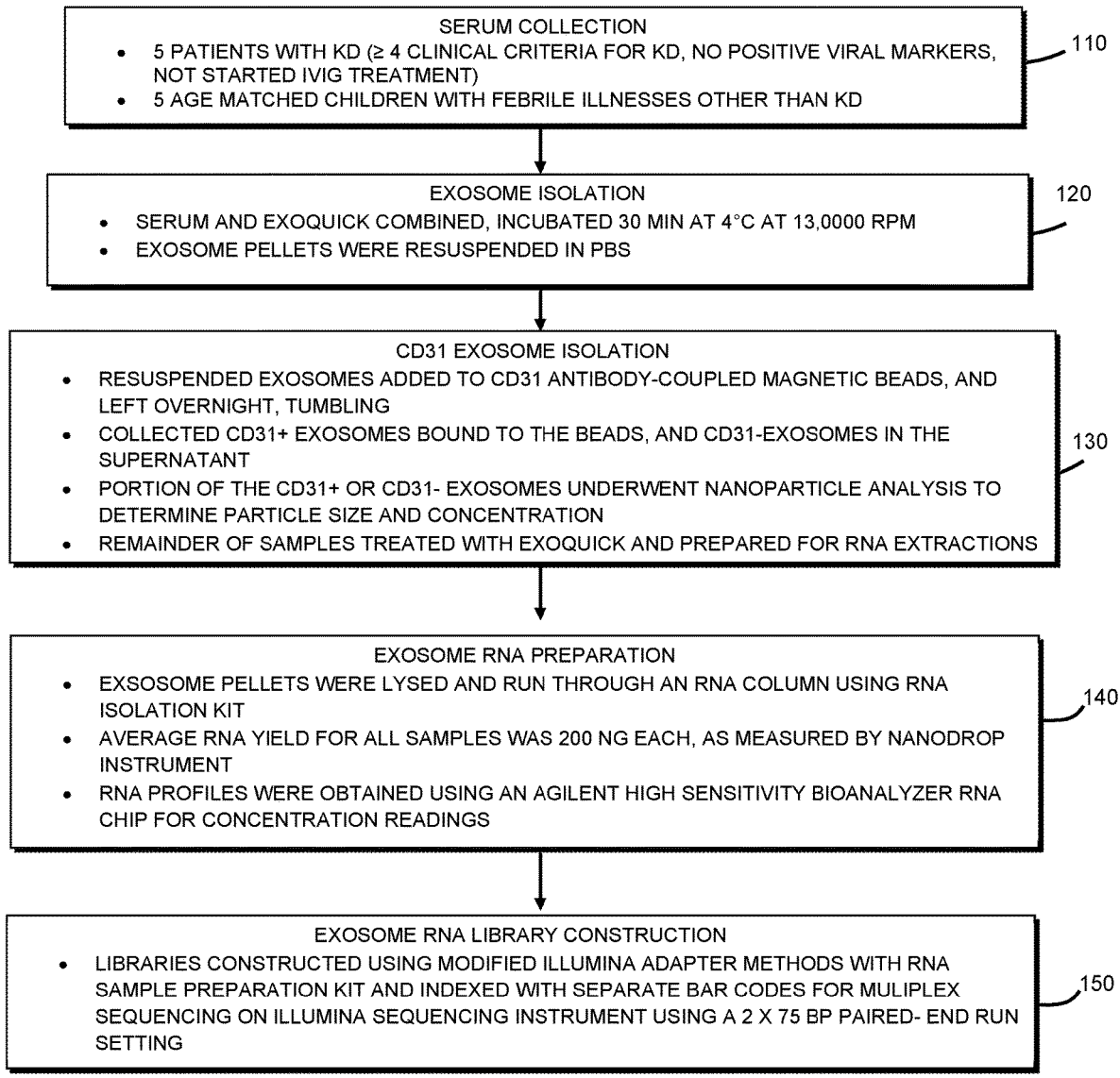
FIG. 1 depicts an exemplary embodiment for the preparation of CD31+ exosome RNA libraries.

Some embodiments of the methods and compositions provided herein relate to the detection of biomarkers for Kawasaki disease (KD), the diagnosis of KD in a subject, and/or the amelioration or treatment of KD in a subject. In some embodiments, a biomarker can include a long intergenic non-coding RNA (incRNA). In some embodiments, the biomarker is present in an exosome-enriched sample from a subject, such as serum.

KD includes an autoimmune disease in which the blood vessels throughout the body become inflamed. This autoimmune disease can be seen in people of pediatric age (ages 24 and under) and affects the several organ systems. Without being limiting, these organ systems can be blood vessels, skin, mucous membranes, and/or lymph nodes. The most serious effects can occur in the heart, where the disease can cause coronary artery aneurysms in children who have not been treated. Signs and symptoms can include, but are not limited to a high and persistent fever in which the fever is not responsive to common care for fevers, bilateral conjunctival inflammation, oral manifestations (for example, erythema, swollen lips, vertical cracking (fissures), "strawberry tongue" (erythema), necrotizing microvasculitis and/or bleeding. In some alternatives described herein, a method of treating, inhibiting, or ameliorating a vasculopathy in a patient in need thereof is provided. In some alternatives, the vasculopathy is Kawasaki disease. In some alternatives, the patient is of pediatric age. In some alternatives, the patient is an adult. In some alternatives, the patient is selected as one suffering from a high and persistent fever. In some alternatives, the fever is at 102° F., 103° F., 104° F., or 105° F. or a temperature within a range defined by any two of the aforementioned temperatures. In some alternatives the fever has persisted from 3 days, 4 days, 5 days, 6 days, 7 days, 8 days, 9 days, 10 days, 11 days, 12 days, 13 days, or 14 days, or any amount of days within a range defined by any two of the aforementioned days. In some alternatives, the fever is at least four days. In some alternatives, the patient has swollen lymph nodes, joint pain, skin rashes, swollen hands and feet, strawberry tongue and/or necrotizing microvasculitis.

"Vasculopathy" as described herein, refers to several types of disorders that can destroy, damage, restrict, impair, reduce, and/or prevent blood flow within blood vessels by inflammation. During vasculopathy, arteries and veins can both be affected. Signs or symptoms of a vasculopathy can include but is not limited to fever, weight loss, livedo reticularis, myalgia, myositis, arthralgia, arthritis, mononeuritis multiplex, headache, stroke, tinnitus, visual loss, myocardial infarction, hypertension, gangrene, nose bleeds, bloody cough, bloody stool, and/or glomerulonephritis. Vasculopathy can include but is not limited to vasculitis, cutaneous small-vessel vasculitis, granulomatosis with polyangitis, Churg-Strauss syndrome, Behcet's disease, Kawasaki disease, Buerger's disease, limited granulomatosis with polyangitis vasculitis, systemic lupus erythematosus, Goodpasture's disease, microscopic polyangiitis, granulomatosis with polyangiitis, Henoch-Schonlein purpura, Cryoglobulinemia, and/or classical polyarthritis nodosa. In some alternatives described herein, a method of treating, inhibiting, or ameliorating a vasculopathy in a patient in need thereof is provided. In some alternatives, the vasculopathy is vasculitis, cutaneous small-vessel vasculitis, granulomatosis with polyangitis, Churg-Strauss syndrome, Behcet's disease, Kawasaki disease, Buerger's disease, limited granulomatosis with polyangitis vasculitis, systemic lupus erythematosus, Goodpasture's disease, microscopic polyangiitis, granulomatosis with polyangiitis, Henoch-Schonlein purpura, Cryoglobulinemia or classical polyarthritis nodosa. In some alternatives, the vasculopathy is an endothelial vascular disease. Endothelial vascular diseases, without being limiting, can include atherosclerosis, collagen vascular disease or pleural epithelioid hemangioendothelioma. In vasculitis, for example, the immune response to the inflammation can block blood flow and cause stroke or heart attack or peripheral ischemia.

"Biological samples" as described herein, can include but are not limited to whole blood, serum, bone marrow, organ tissue, plasma, bodily fluids, urine, or saliva. Bodily fluids can include lymphatic fluid, cerebrospinal fluid, urine, saliva, or ascites fluid. The biological sample can be selected from the group consisting of: whole blood, plasma, serum, urine, cerebrospinal fluid, saliva, lymph, aqueous humor, vitreous humor, cochlear fluid, and tears. More examples of biological samples, which can be analyzed using the methods described herein include peripheral blood, sera, plasma, ascites, urine, cerebrospinal fluid (CSF), sputum, saliva, bone marrow, synovial fluid, aqueous humor, amniotic fluid, cerumen, breast milk, broncheoalveolar lavage fluid, semen (including prostatic fluid), Cowper's fluid or pre-ejaculatory fluid, female ejaculate, sweat, fecal matter, hair, tears, cyst fluid, pleural and peritoneal fluid, pericardial fluid, lymph, chyme, chyle, bile, interstitial fluid, menses, pus, sebum, vomit, vaginal secretions, mucosal secretion, stool water, pancreatic juice, lavage fluids from sinus cavities, bronchopulmonary aspirates or other lavage fluids. A biological sample may also include the blastocyl cavity, umbilical cord blood, or maternal circulation, which may be of fetal or maternal origin. The biological sample may also be a tissue sample or biopsy, from which exosomes may be obtained. For example, if the sample is a solid sample, cells from the sample can be cultured and exosome product induced. In some alternatives, the sample is ascites fluid from a subject, e.g., ascites fluid from a human; cell culture media supernatant from a human primary melanoma cell line; cell culture media supernatant from a human primary colon cancer cell line; or murine macrophage, e.g., murine macrophage infected with tuberculosis. In some alternatives, the biological sample is serum.

"Exosomes" as described herein, refers to cell-derived vesicles that are present in many and mostly all types of biological fluids. Exosomes can be either released from the cell when multivesicular bodies fuse with the plasma membrane or they can be released directly from the plasma membrane. Exosomes have specialized functions and play a key role in, for example, coagulation, intercellular signaling, and waste management. Exosomes can potentially be used for prognosis, therapy, and biomarkers for health and disease. In some alternatives described herein, a method of treating, inhibiting, or ameliorating a vasculopathy in a patient in need thereof is provided. In some alternatives the method can comprise obtaining biological samples from the patient, isolating exosomes from biological samples, extracting RNA from the exosomes, analyzing the RNA contents of the exosomes, wherein the RNA contents are biomarkers, diagnosing the vasculopathy based on RNA patterns from the RNA contents and providing treatment for the patient of their vasculopathy.

In some alternatives, the exosomes have a diameter of greater than 10 nm, 20 nm, or 30 nm; a diameter that is, 30-1000 nm, 30-800 nm, 30-200 nm, or 30-100 nm. In some alternatives, exosomes have a diameter of less than, 10,000 nm, 1000 nm, 800 nm, 500 nm, 200 nm, 100 nm or 50 nm, or any diameter between any two of the aforementioned diameters. Exosomes may also be referred to as microvesicles, nanovesicles, vesicles, dexosomes, bleb, blebby, prostasomes, microparticles, intralumenal vesicles, endosomal-like vesicles or exocytosed vehicles. Exosomes can also include any shed membrane bound particle that is derived from either the plasma membrane or an internal membrane. Exosomes can also include cell-derived structures bounded by a lipid bilayer membrane arising from both herniated evagination separation and sealing of portions of the plasma membrane or from the export of any intracellular membrane-bounded vesicular structure containing various membrane-associated proteins of tumor origin, including surface-bound molecules derived from the host circulation that bind selectively to the tumor-derived proteins together with molecules contained in the exosome lumen including tumor-derived microRNAs or intracellular proteins. Exosomes can also include membrane fragments.

There are several methods for isolating exosomes from a biological sample. Without being limiting, the exosomes can be isolated by centrifugation, differential ultracentrifugation, micro-filtration, gradient centrifugation, single step isolation of vesicles using size exclusion chromatography, lectin affinity, antibody affinity, nanoparticle tracking analysis, microarrays, and immunoadsorption for targeting exosomes. For example, immunoadsorption, or use of agents such as antibodies can be used to target exosomes, as exosomes are known to comprise proteins. Without being limiting, proteins that can be targeted on an exosome with an antibody or portion thereof or a binding agent include, but are not limited to, viral proteins, Fas ligand, MHC I, MHC II, CD44, placental alkaline phosphatase, TSG-I01, MHC I-peptide complexes, and/or MHC II-peptide complexes. In some alternatives, the isolation of exosomes can be performed with centrifugation, differential ultracentrifugation, micro-filtration, gradient centrifugation, single step isolation of vesicles using size exclusion chromatography, lectin affinity chromatography, nanoparticle tracking analysis, microarrays, or immunoadsorption for targeting exosomes. In some alternatives, for immunoadsorption or antibody mediated exosome targeting, a protein on the exosome is targeted, preferably CD31. In some methods, a biological sample selected from the group consisting of: whole blood, plasma, serum, urine, cerebrospinal fluid, saliva, lymph, aqueous humor, vitreous humor, cochlear fluid, and/or tears is analyzed for its exosome components once these exosomes are isolated, enriched, or purified using one or more of the aforementioned approaches. In some methods, the binding agent or antibody, for example, further comprises a detectable moiety. In some methods, the detectable moiety is selected from the group consisting of an affinity tag, colored bead, a photoreactive group, a radionuclide, a hapten, a peptide, an enzyme, a fluorescent species, a luminescent species, a dye, biotin, a triazole, an alkyne, quantum dots (Q dots), and a chelating species.

"CD31", as described herein, refers to platelet endothelial cell adhesion molecule (PECAM-1) which is also known as cluster of differentiation 31 (CD31). CD31 can be found on and within an exosome. In some alternatives, the exosomes are further isolated by targeting a CD31 protein on the exosome. In some alternatives, the CD31 protein is targeted by an antibody or binding portion thereof, or a binding agent. Binding agents, such as antibodies or binding fragments thereof, can refer to a peptide or an affinity molecule. In some alternatives, the antibody or binding portion thereof or binding agent is attached to a solid support, such as a bead, membrane, lateral flow device or a microarray plate. In some alternatives of the methods provided herein, CD31 positive exosomes are compared to CD31 negative exosomes for the presence or absence of one or more markers or signatures.

In some alternatives, a method of treating, inhibiting, or ameliorating a vasculopathy in a patient in need thereof is provided, wherein the method comprises obtaining a biological sample from the patient, isolating an exosome from the biological sample, extracting RNA from the exosome, analyzing the RNA extracted from the exosome for the presence of a marker for a vasculopathy, determining the presence of the vasculopathy based on the identification of the marker and providing a therapy for the patient's vasculopathy. In some alternatives, the determining step further comprises comparing CD31 positive exosomes to CD31 negative exosomes for the presence or absence of markers or signatures or a pattern of markers. In some alternatives, the determining step comprises obtaining nucleic acid from the CD31 positive exosomes and determining the presence or absence of lincRNA by hybridizing a complimentary nucleic acid to a specific lincRNA to a support. In some alternatives, complimentary nucleic acids are specific for linc-ZAF337-1, linc-RMB45-2, lincWDR7-5, linc-CISD1, linc-ADARB2-2, linc-COBL-2, linc-NPVF-2, linc-P2RX4, linc-CXoff36-3, linc-CD180-9, linc-ELMOD1, linc-LAMA1-1, and/or linc-NUDCD2-3.

In some alternatives of the method provided herein, the binding agent specific for CD31 is also joined to a second support or a detection moiety. In some methods, the second support is a plastic, such as a plastic plate or dish, a chip, a membrane, such as a nylon or nitrocellulose membrane, a lateral flow device, a bead, such as an agarose, latex, acrylamide, magnetic, or polymeric bead, a fiber, such as a hollow fiber, or a filter, such as a hollow filter or detection molecule, such as fluorescent dye, colored beads, quantum dots, enzyme etc. Lateral flow devices comprising said support or said detection moiety that comprises said second binding agent are contemplated for use in the methods described herein.

In some alternatives of the method provided herein, the binding agent specific for CD31 further comprises a detectable moiety. In some methods, the detectable moiety is selected from the group consisting of an affinity tag, a colored bead, a photoreactive group, a radionuclide, a hapten, a peptide, an enzyme, a fluorescent species, a luminescent species, a dye, biotin, a triazole, an alkyne, quantum dots, and a chelating species.

In some alternatives, isolated exosomes are further purified by resuspending exosomes in a buffer and adding the isolated exosomes to magnetic beads that are coupled to a binding agent that is specific for CD31. The samples can be separated out and in some alternatives the bead bound exosomes can undergo nanoparticle analysis. A flow diagram as shown in FIG. 1 exhibits several steps, for example, for obtaining exosomes for RNA analysis.

In some alternatives of the method provided herein, the method can comprise obtaining biological samples from the patient, isolating exosomes from biological samples, extracting RNA from the exosomes, analyzing the RNA contents of the exosomes, wherein the RNA contents are biomarkers, diagnosing the vasculopathy based on RNA patterns from the RNA contents and providing treatment for the patient of their vasculopathy. In some alternatives, the RNA can include mRNA, microRNA and/or lincRNA. Long non-coding RNAs (lincRNA) are non-protein coding transcripts. Without being limiting, RNA can be extracted from exosomes by using a commercially available kit for RNA extraction such as Total exosome RNA and protein isolation kit (Invitrogen) or Exosome RNA Extraction kit (HansaBiomed), ethanol extraction from precipitated exosomes, or chloroform extraction. In some alternatives, the RNA is extracted from the exosome by ethanol extraction from precipitated exosomes, or by methods known to those skilled in the art.

There are several types of therapies for vasculopathies. These can include but are not limited to corticosteroids, and/or cytotoxic medicines. In patients with Kawasaki disease these medicaments can include high-dose aspirin, as well as, intravenous gamma globulin. In some alternatives of the methods described herein, the vasculopathy is vasculitis, cutaneous small-vessel vasculitis, granulomatosis with polyangitis, Churg-Strauss syndrome, Behcet's disease, Kawasaki disease, Buerger's disease, limited granulomatosis with polyangitis, systemic lupus erythematosus, Goodpasture's disease, microscopic polyangiitis, granulomatosis with polyangiitis, Henoch-Schonlein purpura, Cryoglobulinemia, or classical polyarthritis nodosa. In some alternatives, the vasculopathy is vasculitis, atherosclerosis, inflammation within arteries, coronary artery vasculopathy after heart transplantation, and/or Kawasaki disease. In some alternatives, the vasculopathy is Kawasaki disease. In some alternatives of the method, once the patient having the vasculopathy is identified utilizing the methods described herein, the patient is given a therapy, which comprises administering corticosteroids and/or cytotoxic medicines. In some alternatives, the corticosteroids are prednisone, prednisolone, and/or methylprednisolone. In some alternatives of the method, the providing a therapy to the patient having the diagnosed vasculopathy comprises administering high-dose aspirin and/or intravenous gamma globulin. In some alternatives, the intravenous gamma globulin is administered to the patient at 2 g/kg as a single infusion. In some alternatives, the aspirin is administered to the patient at 3, 4 or 5 mgs/kg per day or any dosage in between any two of the mentioned values. In some alternatives, the aspirin is administered to the patient 80, 85, 90, 95 or 100 mgs/kg per day or at a dosage that is in between any two of the mentioned values. In some alternatives, the aspirin is administered to the patient 30, 35, 40, 45 or 50 mgs/kg per day or any dosage in between any two of the mentioned values. In some alternatives, the patient may be experiencing hepatic toxicity and the patient is administered 2, 4, 6, 8, 10, 12, 14, 16, 18, 20, 22, 24, 26, 28, 30 mgs/kg per day or any dosage in between any two of the mentioned values.

In some alternatives, the analyzing further comprises identifying the RNA in the isolated exosomes. In some alternatives, the RNA is lincRNA. In some alternatives, the linc RNA is identified as linc-ZAF337-1, linc-RMB45-2, lincWDR7-5, linc-CISD1, linc-ADARB2-2, linc-COBL-2, linc-NPVF-2, linc-P2RX4, linc-CXoff36-3, linc-CD180-9, linc-ELMOD1, linc-LAMA1-1, and/or linc-NUDCD2-3. In some alternatives, primers specific for linc-ZAF337-1, linc-RMB45-2, lincWDR7-5, linc-CISD1, linc-ADARB2-2, linc-COBL-2, linc-NPVF-2, linc-P2RX4, linc-CXoff36-3, linc-CD180-9, linc-ELMOD1, linc-LAMA1-1, and/or linc-NUDCD2-3. In some alternatives, the lincRNA is identified by complementary binding to a complimentary nucleic acid that is immobilized to a chip or to a bead. In some alternatives, complimentary nucleic acids are specific for linc-ZAF337-1, linc-RMB45-2, lincWDR7-5, linc-CISD1, linc-ADARB2-2, linc-COBL-2, linc-NPVF-2, linc-P2RX4, linc-CXoff36-3, linc-CD180-9, linc-ELMOD1, linc-LAMA1-1, and/or linc-NUDCD2-3.

In some alternatives, the analyzing further comprises preparing or constructing an exosome RNA library for analyzing the RNA in the exosome. In some alternatives, constructing the RNA library comprises attaching a cloning linker to the 3' and 5' ends of the isolated and purified RNA from the exosome for cDNA synthesis and amplification. In some alternatives, the library can be constructed by using modified adaptors with an RNA sample preparation kit in which the RNA is indexed with separate barcodes for multiplex sequencing. In some alternatives, the RNA contents from the exosomes of a patient in need comprises more lincRNA when compared to a control individual lacking symptoms of a vasculopathy. In some alternatives, the linc RNA is identified as linc-ZAF337-1, linc-RMB45-2, lincWDR7-5, linc-CISD1, linc-ADARB2-2, linc-COBL-2, linc-NPVF-2, linc-P2RX4, linc-CXoff36-3, linc-CD180-9, linc-ELMOD1, linc-LAMA1-1, and/or linc-NUDCD2-3. In some alternatives, primers specific for linc-ZAF337-1, linc-RMB45-2, lincWDR7-5, linc-CISD1, linc-ADARB2-2, linc-COBL-2, linc-NPVF-2, linc-P2RX4, linc-CXoff36-3, linc-CD180-9, linc-ELMOD1, linc-LAMA1-1, and/or linc-NUDCD2-3.

"Biomarker" as described herein is indicator that can be a measurable indicator of the severity or the presence of a disease state. A biomarker can be a specific cell, molecule, gene, gene product such as an RNA, enzyme, protein or a hormone or other markers known to those skilled in the art that is correlated with a disease or disease severity. In some alternatives described herein the biomarker is within an exosome. In some alternatives the biomarker is a gene product. In some alternatives the biomarker is a protein. In some alternatives the biomarker is correlated to a vasculopathy. In some alternatives, the biomarker is correlated to Kawasaki disease.

Previous research has explored the genetics underlying KD, as well as KD patients who are unresponsiveness to IVIG therapy. However, the pathogenesis of KD and patients' varying responses to treatment remain unclear. Although some susceptibility genes have recently been identified, this line of research is relatively immature, and not yet applied in the clinical setting to aid in early diagnosis or screening of patients.

There is a growing interest in clinical applications of exosomes, which contain proteins, lipids, metabolites, and RNA (mRNA, microRNAs, and lincRNAs) reflective of their originating cell. It is becoming increasingly clear through transcriptomic and proteomic profiling that exosomes have specialized functions and play a key role in several important bodily processes (e.g., coagulation, intercellular signaling). Some research has examined the relationship between exosomes' cargo molecules and presumably related biological effects, and a few studies have reported diagnostic and prognostic value of exosomes. Recent studies have also investigated microRNA profiles of exosomes from KD patients before and after IVIG therapy. However, no other studies to date have implicated CD31-positive exosomes or their contents in KD, or in other vascular injury.

From the alternatives described herein, it is contemplated that there would be a difference in CD31-positive exosome RNA profiles between individuals with KD versus those without the disease, but it is also expected that the expression pattern for patients developing coronary artery disease despite IVIG treatment should differ from those not responding to therapy. This would allow physicians to identify high-risk KD patients and make more timely decisions about their further treatment.

These CD31-positive exosome expression patterns could also be used to identify other types of vascular injury, and track their progression. Examples include but are not limited to coronary artery vasculopathy, which occurs after heart transplantation, or identifying atherosclerosis and inflammation within arteries.

The CD31-positive exosome pattern or "signature" or "marker" or its components, could potentially serve as specific diagnostic and prognostic biomarkers for Kawasaki disease. These exosome expression patterns could also be used to identify other types of vascular injury, and track disease progression. Examples include but are not limited to coronary artery vasculopathy, which occurs after heart transplantation, or identifying atherosclerosis and inflammation within arteries. In some alternatives, the signature or marker for Kawasaki disease in CD31 positive exomes are lincRNA. In some alternatives, the lincRNA comprises linc-MBOAT7, linc-ZNF337-1, linc-RBM45-2, linc-WDR7-5, linc-CISD1, linc-ADARB2-2, linc-COBL-2, linc-NPVF-2, linc-P2RX4, linc-CXorf36-3, linc-CD180-9, linc-ELMOD1, linc-LAMA1-1 and/or linc-NUDCD2-3.

Certain Methods of Therapy

In some alternatives, a method of treating, inhibiting, or ameliorating a vasculopathy in a patient in need thereof is provided, wherein the method comprises obtaining a biological sample from the patient, isolating an exosome from the biological sample, extracting RNA from the exosome, analyzing the RNA extracted from the exosome for the presence of a marker for a vasculopathy, determining the presence of the vasculopathy based on the identification of the marker and providing a therapy for the patient's vasculopathy. In some alternatives, the vasculopathy is vasculitis, atherosclerosis, inflammation within arteries, coronary artery vasculopathy after heart transplantation, and/or Kawasaki disease. In some alternatives, the patient is of a pediatric age. In some alternatives, the patient is 0 years, 1 year, 2 years, 3 years, 4 years, 5 years, 6 years, 7 years, 8 years, 9 years, 10 years, 11 years, 12 years, 13 years, 14 years, 15 years, 16 years, 17 years, 18 years, 19 years, 20 years, 21 years, 22 years, or 23 years, or any age defined between any two mentioned values. In some alternatives, the patient is of an adult age. In some alternatives, the patient is febrile. In some alternatives, the fever is at 102° F., 103° F., 104° F., or 105° F. or a temperature within a range defined by any two of the aforementioned temperatures. In some alternatives the fever has persisted from 3 days, 4 days, 5 days, 6 days, 7 days, 8 days, 9 days, 10 days, 11 days, 12 days, 13 days, or 14 days, or any amount of days within a range defined by any two of the aforementioned days. In some alternatives, the fever is at least four days. In some alternatives, the isolation of the exosome comprises selecting and/or isolating an exosome that comprises CD31. In some alternatives, the method further comprises preparing an RNA library from the RNA of the exosome. In some alternatives, the analyzing comprises identification of an RNA pattern of CD31+ positive exosomes. In some alternatives, the therapy comprises administering intravenous gamma globulin to the patient. In some alternatives, the RNA comprises mRNA, microRNAs and/or lincRNA. In some alternatives, the RNA contents from a exosome of the patient comprises more lincRNA when compared to a control individual lacking symptoms of a vasculopathy. In some alternatives, the biological sample is whole blood, serum, plasma, urine, saliva, lymphatic fluid, or cerebrospinal fluid. In some alternatives, the method further comprises comparing CD31+ and CD31− exomes for the presence or absence of specific RNA's.

In some alternatives, a method of treating, inhibiting, or ameliorating a vasculopathy in a patient in need thereof is provided, wherein the method comprises obtaining a biological sample from the patient, isolating an exosome from the biological sample, determining the presence of CD31 on the exosome, identifying the presence of a vasculopathy in said patient based on the identification of CD31 on the exosome and providing a therapy for the patient's vasculopathy. In some alternatives, the vasculopathy is vasculitis, atherosclerosis, inflammation within arteries, coronary artery vasculopathy after heart transplantation, and/or Kawasaki disease. In some alternatives, the patient is of a pediatric age. In some alternatives, the patient is of an adult age. In some alternatives, the patient is febrile. In some alternatives, the therapy comprises administering intravenous gamma globulin to the patient. In some alternatives, the presence of CD31 on the exosome is determined by binding an antibody specific for CD 31, a binding portion of an antibody specific for CD 31 or a binding agent specific for CD31 to the CD31-containing exosome. In some alternatives, the exosome and/or the antibody, binding portion of an antibody, or a binding agent is/are attached to a solid support, such as a bead, membrane, lateral flow device or a microarray plate.

In some alternatives, the biological sample is whole blood, serum, plasma, urine, saliva, lymphatic fluid, or cerebrospinal fluid. In some alternatives, the method further comprises comparing CD31+ and CD31− exosomes for the presence or absence of specific RNAs.

Also, it is contemplated that one may compare CD31+ to CD31− exosomes for the presence or absence of one or more markers.

In some alternatives, a method of treating, inhibiting, or ameliorating a vasculopathy in a patient in need thereof is provided. The method can comprise obtaining a biological sample from the patient, isolating an exosome from the biological sample, extracting RNA from the exosome, analyzing the RNA extracted from the exosome for the presence of a marker for a vasculopathy, determining the presence of the vasculopathy based on the identification of the marker and providing a therapy for the patient's vasculopathy. In some alternatives, the vasculopathy is vasculitis, atherosclerosis, inflammation within arteries, coronary artery vasculopathy after heart transplantation, and/or Kawasaki disease. In some alternatives, the patient is of a pediatric age. In some alternatives, the patient is of an adult age. In some alternatives, the patient is febrile. In some alternatives, the isolation of the exosome comprises selecting and/or isolating an exosome that comprises CD31. In some alternatives, the method further comprises preparing an RNA library from the RNA of the exosome. In some alternatives, the analyzing comprises identification of an RNA pattern of CD31+ positive exosomes. In some alternatives, the therapy comprises administering intravenous gamma globulin to the patient. In some alternatives, the RNA comprises mRNA, microRNAs and/or lincRNA. In some alternatives, the RNA contents from a exosome of the patient comprises more lincRNA when compared to a control individual lacking symptoms of a vasculopathy. In some alternatives, the biological sample is whole blood, serum, plasma, urine, saliva, lymphatic fluid, or cerebrospinal fluid. In some alternatives, the method further comprises comparing CD31+ and CD31− exosomes for the presence or absence of specific RNAs. In some alternatives, the RNA is lincRNA. In some alternatives, the RNA is the RNA is ZAF337-1, linc-RMB45-2, lincWDR7-5, linc-CISD1, linc-ADARB2-2, linc-COBL-2, linc-NPVF-2, linc-P2RX4, linc-CXoff36-3, linc-CD180-9, linc-ELMOD1, linc-LAMA1-1, and/or linc-NUDCD2-3.

In some alternatives, a method of treating, inhibiting, or ameliorating a vasculopathy in a patient in need thereof is provided. The method can comprise obtaining a biological sample from the patient, isolating an exosome from the biological sample, determining the presence of CD31 on the exosome, identifying the presence of a vasculopathy in said patient based on the identification of CD31 on the exosome and providing a therapy for the patient's vasculopathy. In some alternatives, the vasculopathy is vasculitis, atherosclerosis, inflammation within arteries, coronary artery vasculopathy after heart transplantation, and/or Kawasaki disease. In some alternatives, the patient is of a pediatric age. In some alternatives, the patient is of an adult age. In some alternatives, the patient is febrile. In some alternatives, the therapy comprises administering intravenous gamma globulin to the patient. In some alternatives, the presence of CD31 on the exosome is determined by binding an antibody specific for CD 31, a binding portion of an antibody specific for CD 31 or a binding agent specific for CD31 to the CD31-containing exosome. In some alternatives, the exosome and/or the antibody, binding portion of an antibody, or a binding agent is/are attached to a solid support, such as a bead, membrane, lateral flow device or a microarray plate. In some alternatives, the biological sample is whole blood, serum, plasma, urine, saliva, lymphatic fluid, or cerebrospinal fluid. In some alternatives, the method further comprises comparing CD31+ and CD31− exosomes for the presence or absence of specific RNAs. In some alternatives, the RNA is lincRNA. In some alternatives, the RNA is the RNA is ZAF337-1, linc-RMB45-2, lincWDR7-5, linc-CISD1, linc-ADARB2-2, linc-COBL-2, linc-NPVF-2, linc-P2RX4, linc-CXoff36-3, linc-CD180-9, linc-ELMOD1, linc-LAMA1-1, and/or linc-NUDCD2-3.

Identification of Signatures of Kawasaki Disease in a Subject

In some embodiments, exosomes are isolated from a patient that is febrile who is of pediatric age from a biological sample such as whole blood, serum, plasma, urine, saliva, lymphatic fluid, or cerebrospinal fluid. Using a total exosome RNA and protein isolation kit RNA is recovered and exosome RNA sequence analysis is then be performed using a Maverix Biomics instrumentation and software (Exosome RNA-seq Analysis 1.8). Use of the software allows the user to select the sequencing platform that was used to generate your raw RNA-seq reads. Choices include Illumina (NextSeq 500, HiSeq 2500, HiSeq 2000, MiSeq, Genome Analyzer IIx) or Ion Torrent (Proton). This information is used to choose the correct adaptor sequence to use for trimming and filtering as well as to select the correct quality thresholds for filtering and trimming. Expression of lincRNAs of interest can also be obtained. The linc RNAs of interest that can be found as signatures for Kawasaki disease are linc-ZAF337-1, linc-RMB45-2, lincWDR7-5, linc-CISD1, linc-ADARB2-2, linc-COBL-2, linc-NPVF-2, linc-P2RX4, linc-CXoff36-3, linc-CD180-9, linc-ELMOD1, linc-LAMA1-1, and/or linc-NUDCD2-3.

Detection, Diagnosis and/or Treatment of Kawasaki Disease

Some embodiments of the methods and compositions provided herein include determining and/or detecting the presence or absence of a KD biomarker in a subject, such as a sample from the subject, such as a serum sample. As used herein, "subject" can include a human or a non-human mammal, e.g., a dog, a cat, a mouse, a rat, a cow, a sheep, a pig, a goat, a non-human primate or a bird, e.g., a chicken, as well as any other vertebrate or invertebrate. In some embodiments, a subject can include a patient, such as a patient having KD. In some embodiments, the subject can be a pediatric subject, such as a subject is less than 25 years old, less than 20 years old, less than 15 years old, less than 10 years old, less than 5 years old, less than 3 years old, or less than 1 years old, or any age between any two of the foregoing ages. In some embodiments, a subject can have symptoms of KD, such as febrile symptoms, or any symptoms of KD described herein.

In some embodiments, a KD biomarker can include a long intergenic non-coding RNA (lincRNA). Examples of such lincRNAs include linc-MBOAT7, linc-ZNF337-1, linc-RBM45-2, linc-WDR7-5, linc-CISD1, linc-ADARB2-2, linc-COBL-2, linc-NPVF-2, linc-P2RX4, linc-CXorf36-3, linc-CD180-9:copy2, linc-ELMOD1, linc-LAMA1-1, and/or linc-NUDCD2-3. In some embodiments the lincRNA is linc-MBOAT7, and/or linc-ZNF337-1. TABLE 1 lists example DNA sequences encoding such lincRNAs, and include the lincRNA name (gene ID), and human chromosomal location of the DNA encoding the lincRNA. Some embodiments include detecting one or more lincRNAs in a sample, such as a lincRNA listed in TABLE 1. Some embodiments include determining and/or detecting the presence or absence at least 1, 2, 3, 4, 5, 6, 7, 8, 9, 10, 11, 12, 13, 14, 15, 16, 17, or any one of the foregoing numbers, of lincRNAs in a sample, such as a lincRNA listed in TABLE 1.

TABLE 1

| Gene ID [Chromosome location (start→stop)] | [SEQ ID NO.] Example DNA Sequence encoding the lincRNA |
|---|---|
| linc-MBOAT7 [chr19 (54703321→ 54703838)] | [SEQ ID NO: 01]<br>GCTAATTTTAAATTTTTAGTAGAGACGGGGTTTTGAACTCCTGGTCTCCAAC<br>GCCTGACCTCAAGTGATCCACCCGCCTCAGCCTCCCAAAGTGCTAAGATTACA<br>GCTCGTGTTCTTCAGTTGTCTTCCCTACGCTGCTGCCTCGGCAGTCACTATCTC<br>CTCAGGAAGCAGTCCCACCCGCCCCTTTCTCTTCCACGGCATCCACACCATCC<br>GGATGCCTGGATTCAAATGCCACGTCACCACTTGCCAGCTGCAGTGCCTTCGA<br>CAAGTTTCTCAATCACTCTGTGCCTCAGCGTCCTCCTCTGTAAAACGGCGAAT<br>GATGGTAGCGCCTACCTCATAAGCTTGTGAGGATTAAGTGAGAGTCTATCCA<br>GTGTTGAGGAGAGTGGCATAAATAAAGCGCCTAGTGGTA |
| linc-ZNF337-1 [chr20 (25989427→ 25991167)] | [SEQ ID NO: 02]<br>CCTGGAAGCCCGCTGGTCACACAAAGGACAAAGGCATTTCTATGTTGGGCCT<br>CGGTCCCTTATCAGTGCAGCTGAGGAATGTCTTTAGGACAACCCCCTTTGCTA<br>GTTTTCCTTCTCTGTGCCTGCAGCCTGATTTTTCTGGCTGTTTCTCTGTTTAAAG<br>GAGTTTTACCAAGGACCCGCTCTAACTCCCTAAAGGTTTTTTTCTCTCAAGGG<br>GACACACAAAGTTCCAATCACACACATGCCTCCCTATATCCACTTACCCTCTGC<br>CTCACAGCCAAATAGATGCTCTGGTACGGTCAGCGTCTAAAGATTTTACAAAC<br>AATATCTCTTCTTCTAGTTTGCAGTCATTATTGAAATAACAAACATGTCCTATT<br>GTCAGGCCTTACTCTCAGTAACTGATTTCATTGATCTGAATAGGAAACTTACTT<br>GATTAATCAGCTACTCTTTGGTATTACCTGACATCTCATTAATGCATCTTTGAA<br>TTGAATTATTGCTCAATAGGAGTGATTGTGAAATAGTGGCAATGTATTACATC<br>ACTATTG |
| linc-RBM45-2 [chr2 (178417963→ 178424476)] | [SEQ ID NO: 03]<br>TAATAATGCTGGCTTTTGGTTTAGTTTCAGTAAAAGAACCGGGATGGCAAAA<br>GGCTTACAGCTGGAAGGAACTTGCTATGAGTCTTAGATGAGACTTTGGACTT<br>TTGTTGCTGGAGCAAGTTAAGACTTTTGGGACTACTGGAATGGAATGATTGT<br>ATTTTGTATATGAGAAGCACATGATTTTTTTGAGGCTAGGGGCAGAATGCTAT<br>ATTTGCATATGTTCATCACCATCAAAACTCATGTTGAAATGTTATTTTCAGTGC<br>CGCAGTATAGGGAAATGGAGCCTAGGGGAGCTGTTTGGGTCAAGGGAATGG<br>ATCCATTATGAATGACTTGGTGCTGTTCTCGCAGTAGTGAGCTCTTGCTCTCAT<br>GAGACTGGATTATTCTCATGGAAATGGATTAGTTCCCATGAGAGTGGGTTGT<br>TATAAAGCAAGATGCTCTTGGGTTTTGCCCCTTTGCACATGTCTGCTTCCCCTT<br>TGACCTTCTGCCATGTTATGATGCAGCACAAAAGCCCTCACCAGAAGCCAAGC<br>TGATGCTGGCACCGTGCTTCTTGTACTTCCCAGCCTGCAGAACCATGAGCTAA<br>ATAAACCTTTCTTATAAATTATCCAGTCTGATGTATTATGCTATAGCAACACAA<br>AATAGACTAAGACGGGTGTTATTATCCAAATTAATTTTATTAGGCAGAACACAA<br>TCACATGATTTATACAAAGGAATTAGCAGAGAAGACACAGTTTTCGGTACTAC<br>CGTTGAAAAATTTGTTCCTCAGAGTTGGAGTGTGCTGTGGGATACACTAATG<br>GGGATGTTACACAGATTATTTTAGCATGTTTTACTGCTTTCACTTCTAAGAGGT<br>AAGCGACATTGAAGTATCATGTCTTTCCTCCAGACTGGAACCTTTCATGGTCA<br>GAGATATCCTGTTAATGCCTGTTTTTATTTCTGCAATAAAGCCATGAAAGTAA<br>TAAATTGGATGGGAAGGATCTTTGAGGCCAATGGTCAAAATATAAGATTTCC<br>AAAAGAAAAATGTCATCAGCCTGTAGGAACACATGTTCTGGCTTGC |
| linc-WDR7-5 [chr18 (53497615→ 53506331)] | [SEQ ID NO: 04]<br>AAAACATTTGCTGACTGCTGTTCTATCTAGGATATCATCAGTGTGTAGATGAT<br>CAGAGTTCATGTCAGTGTTCCTACAAGCCAATGAAGAAAACAGAGATCTGT<br>GTTCTGAATGGAAAAATTCCTACTGATGCCAGTAAGTGAGCCATCCATCTATG<br>ATGTGTCTATGGGGAAGAAAGTGACATGAATGAGTAAAATAGAATATATGCT<br>TTAAATCATGAAAATTGAGTCCAGATGGAAAGGTTAGGAGGAAATGGAGTG<br>GAAAGGTGGATGAAGAAGAGTGAGAACTCATGCAGTCGTTGCGCACTTGGTT<br>GACACTTCCTTCCCTGTGACTACAATTCCAAGTTCAGTACTCCTGAGCTTTTAT<br>AGATGGATGAGAATATAGGGGGAAGAAACAAGAGGAAGGAGTTTTCTGAA<br>ATCTCGGTGGAGAGGAGGGAGAAAAAAGATGGGAAAATGTTACAAGCATTC<br>TGTTCATGTTGTATCACTTAGTGCAGTCTTGTCTTCCCAGCCCACTAGTCTGGA<br>ACAAGTCAGTCTCAAACATAACAACAGACACTGGGGAGCTCTCCAACAAAAG<br>ATCACCTCCCAAAGAACAGGATGGTGTCGAAGACTGAATGCCAGCCTGAGGA<br>AACAGAAATACTACAGAAGCACGCCAGAGCCTGCAGTGTCTCCTCGCTGCCT<br>CTCAATGAACTGCTAAAAGACCAAGAACTCTGCTGAGAGATAAGAAGAGGG<br>GAGGGTGTGCTGCAGGTGGTGCTGGGAGGCCCAGACCTTCTCCTGACATCTG<br>GGGCTGGCTACAGGAAACAGAAACATCACCCAGGCCTTGGCGCGAGACAGG<br>ACAGAGGCAGATTGTGACTCAGATCTGCAGGTGGAAAGTGGGCCTTTCGTTT<br>TCTCCTAGGGGTAGAGCAAAGCCAGAGGGCTCAGTCAGAGGAAACCTAAGG<br>CAGTTCATGATCCCTTCAACTTTATACCATTTCCTCAAAACTGCCTCCAAACAG<br>TGGGCAACTGGAAAGGTGGTCTGACCTCCAGTGATCACACAGTATGCATTAT<br>AACAGAAGGCTGTCACTGTCAATTGCATGGCTCCCTCACTATGCATTCCTTCT<br>ATCAATTTACGACAACACACTGTAGTGAGTACCTGCACATTGCTGGGTATTTT<br>GGCAGACATTGATAGTAGATGAATAACACCTGGTACTTGACCTTGAGACGCT<br>CACTGCCTAGTGTGGGGAACCAATGGTTGCAATATAAAGTATTAACTAGAGG<br>GATAGAGGACTGCCTGAGGATCTCTGCACTCAGAGGAAGGGCCATGAGATC<br>AGCCAGGACAGTAGGGAGGCAGTGACTCATGAAATTAGCAAGTGGTGAGAA<br>GAGGGCA |

TABLE 1-continued

| Gene ID [Chromosome location (start→stop)] | [SEQ ID NO.] Example DNA Sequence encoding the lincRNA |
|---|---|
| linc-CISD1 [chr10 (58058713→ 58074528)] | [SEQ ID NO: 05] CAAGCATACACATTTTTATAACCAAATTAGGAATATTGATTTTAAAAATCTTCA AATTTCCTTACAATATATAGTAGGTGTCCCCAACCCCTGGGCCACAGACTGGT ACCACGCTGCAGACTGGTAGCTTTCTGTGGCCTGTTAGGAAGTGGGCTGCAC AGCAGGAGGTGAGTTGCAGTTTAACTAGCATTACCGCCTGAGCTCCGCCTCC GGTCAGATCAGCTGGGCATTAGATTCTCACAGGAGCAAGAATCCTATTGGGA ACTGTGCGTGAGAGGCATCTAGGTTGCACTCTCCTTATCAGAATCTAACTAAT GCCTGATGATCTGAGGTGAAATAGTTTCATCCCGAAACTACCCCCGACTCTGT CTGTGGAAAAACTATCCCCACAAAACCTGGTGCCAAAAGATTGGGGACCAC TGATATGTAGGGTTCCAATTATTTTGGAAGACATGAATTAAGAGACTGGTTG AAGTTCACTAGGCGTTCTTTGCTTCTAAGTCCTCTGTCCTCTAGGCTGTGTTGC ATACATAATAATGCAAGACTGGAGGACACCAATAGCATCTGCAAATGACAAG ATACCTTCAGATGAAGCCTAATTCCAAAAAGATTAAATAGTTATCCACATGTA GATTATATAAACTTTTAGGAGGTTAATTCTGTGGGTTGCTGGATTCTGGCTCC CTTATGCCCTGCAACCTTATGGCTTCATGCTATATATGAACTTCTTACTAGGAA TAATGGATGACTTGACTGTTCTCTGCTTCCTGAACAACTTCTACCATCATGTTA AATTGAAGCTTCTCAGTTATGCCAAGTTATTCAATATATGATGTCCTATGTTCC TCATCTTTGCACTGGAAATAATGCTGTCAACTCAAATGCTTGATCAAAGTAT TGATTATCTGGTGTCAGCTGTTTTCCTGAATTCATGCAGTACTGACAAAGAAG AATTTGGAATTAAATACCAGAGAAGAGTTCTATTCCACCTAGAGGGTACAGTT TTGTGACAATATTTTTGACATTCTAATTAGGTTATCAGCCTATGATTGCAAATA AAAAATGAAACAATAATAATATTTAAATACAAAGGTATTTAAAGTAATGAAA GCAAAAGTCTAATGTACATCTTTAGTTCTTTTTTCATAGCTGAGTTAATAAATA CTTTTTGTATCAAGTTAATTTGATATAAAAAGTAATTCTTATATATTACTAATC AAGATAATATGAATTCAACAAAGCATTACTTAGAAATATAATATTAAAATGC AACAGCTTTAAATCCTATTGACCCAATGGATATTACCTACAAGTCAGGCTCTG TACAAACCCATTCAGAATGCTCCAGCTGACAGTGCAGTATTTTATGCCAATCA AATTATGTTATTGTGATAGAACATGATATGGATTTTTAAGAAAAAAATGATCC AATACAAAACTGTTATATACTTGGCCCTCATCCCCATGATCACAAATCCCAGA ATTTCAAGAAAATTTGGCCAACTGAAGTAAATTGTAAATTGTGTTTACACTGT CACATAGGTGGCATCACTATAGCTAAGACACAAAGTATTCTCTGTGTATTGTC AAGATTATCCTGAAATACCATAATTTTTAAAAGTTTTCAGGACATATCTATTTA TCTAATGTTATATATATTTAAATAAAATATCTATACTATTTTAATATATACCTTA ATTTTCTCTGCTATGTGTTTAATTCTGTCATGTAAAAAAGAGACACGAAAATT GTAACCCCCAGCACCTTAGAATGTGAACTTATTTGAAAATGGAATCATCACAG AGGTAATCTGGTTGAAATGAGCTCATTAGGATAGACGGTAATCCAATATGAC TGGGCTACTTATAGAAAAGAGAAAATTTGGACACAGATAGCACATAGAGG GAAGATGATGAATACACAGAGAATGCCACTGAAGATGGAGGTAGAG ATTGCAATTATGTTGCCACAAACCAAGGAACATCTGGGATTGCCAGAAGCAG GAAGAGGCAAAGAAGTAACCTTCTCTACAGGTGTTAGAGGGAGCATGGCCC ATCAATCCCTTGATTTCACACTTCTAGCCTTTAGAACTATGAAACAAAACTTTT CCCTTGTTCTAAGACATCTAATGTATAATACTTTGCTATTGCAGCCATAGGAA GCTATACCTTCTTTCCTTCACTATTAAAAATTTTATTGTTCTCTTTCAACTCCTTT GACATCATGTCTATTCCTTTATAACTAAAGTCAATGATTAATTAAAGAATAATA TCTCTTTCTAAGTGTAAGGTTGTGTTCCAACTGTCTTACATACATTAATTCATTT AATTCTTACAACAACCCTGTGAAGTAAATACTATTATTTTGCTTTTTAC |
| linc-ADARB2-2 [chr10 (2211334→ 2218626)] | [SEQ ID NO: 06] CTCCCTGCAGCATTTTTAGAAGGTACCAAATAAGAAAAACGTGGATGAAGAT GGAGAAAGCATACAAAACTTTTACACACTGGTTTGAAGGGCAAGCCGTTGTA CATTCCTTGAAGTCAGGTGCTCTGCTCAACAGAAGGTGTGCTGAATAACGTTA CAGGCTCTGTTCCCGGGAGACGTGGAAGCTGTCACCGCGCGGAACATAAAG AACAGGCCAAGACCAGTGCAGGCATCGACGACTTTCTCCATTCAGAGCCTCC GCGCATCCCAAATAAATAAACACATCAAAACGTGCAAA |
| linc-COBL-2 [chr7 (54643745→ 54646487)] | [SEQ ID NO: 07] GGTGACACTGGATTCTCTCCATCATGGAGGGGTGGGCCTTTGCTTGGGAAA ACACAGGCTTTCTGCATGTGGGTTTTCCTCTCTATGATCGTGCTTTTGCCGGCA CTATTATCCCAACATTGCCTCTGATTAATGTGCTTATTGCACAGAGGACATGC GTTGAAGGACTCAGGCCCAGAGGACTCACCATACTACACCTAGCTTCCCTCTC ACCCAGAAGCAGCTAACCTGATGAAACAAATGCCCTGGCCTTGGGAAGACTT AGCTATATCCTAATTGGAGCCAACACCCAGAAAAAAAGAAGCACTGTCCTAA AGATAGTAGATGATTTGAATCAGCGTGTGATATGGGTGCTGATTTTTCCAA AGCTTGAATATATGGGTCCAGGAATCAAGGACCAAGTGGGAGTGTTTTCTCC ACTATTACACAAGATTTCTCACTTACAGAATTTTTATATTCTTCCTCTATCAAGC TCTACTACCTTTGGTTCCAACGGAAACATGCCTGTACCAGGGCCAGCACCCTC GAACAGTGACTGACAGGAGCTGGTATTTATATATTCCAGATTCTTCTTTGGCT GGAGACAACCCTGAGGTGTGTTTCATGCTATCTGAAACCCCCGTGGGATT AAACTCCTGTTGCATGTAGTGGTAACGAGTTTGATAACACATTCTGCCTACAT TTTTTTAATCTTATTTCCTCCTCCTCTACTGGTGGTTCCTGAAACTCTTAAATAA ATTGATTAGACTCAAA |

TABLE 1-continued

| Gene ID [Chromosome location (start→stop)] | [SEQ ID NO.] Example DNA Sequence encoding the lincRNA |
|---|---|
| linc-NPVF-2 [chr7 (26097439→ 26101262)] | [SEQ ID NO: 08]<br>TAGCAACTCCACATTTTTTATTCACTCACAAAGACACATGGTCATAAATAAAA<br>TGCATGGAACCAGCGAGACAATAGCACAGCAGTAATGTCATTTTATATGCAG<br>CATGGCCCTGTTGTGAACGGAATGATTGTGAACGGAATGATGGCCAAGGAG<br>CTTTATGCTTCTGCACCGCCAGCTCACACGATGGTCCGTGTATTGCCCCGTGG<br>AAAACCGGGGGTGGAAAGCTGTCTCCACGTTCTGCTGCCGAAGCAGCAAGCT<br>GATTCACACATCTTGAAGGCACAGTGGAACATGGAAGGGTGCATATGAGACT<br>TGATTTTGAGGATGAAACTTCCTGTCTGAATCGCTAAGTCTCCCAGCAGGGGT<br>GTTAATGTCCCTGTGAGATGCAGGCTTCCCACAGACACACCCAGGTTGCGAG<br>TGGGTTCAACATGGTCACAGGAGCTTCAAATGGTAAGATGGCAAGATCTGGT<br>AGCATACTGAGACCACCAACCAGGAATGGAGGCTTGCTCCCAAGTAACTAAA<br>CATGGACTTGTCTCTGACACGGAAACAATGTGAAACACAGAAGGCTTTTGAG<br>ACTCAGAGGCACTCCAACAATGATACTTGAAAACCAGAACAGAGTTTGACAC<br>AGATGGATGCTTTCCAAATGTCATGTCATTTTTTCATATGTCAAGGGCGACCC<br>AATGTTTGCTTCCTGTTCCCTAGGTGGGTTTTCCATGGGACTGCTTCTAACCC<br>CCAATCCCCACACACTCCACCTGGGCTGAAACTGCTGCCTCTTTTCCAATATAT<br>AGAAAGAAATGTGGCTCCACCCTGCATTTCCGTAAGACTCAGCTAGTTACAAA<br>TTTAGAACCTTGGAAACAATGATAAAACATTCTTCAAGAGAAATAATCTCCA<br>GGTTTTGTTTCATTATCTGTGAGACTATTCAGTGCTACATCTGCTGAAGGGCA<br>TAAAATCCATATTTTGTTTTAAAAATGGGTCTACTTTGATGCAGCACCCAAAT<br>TTAATTACTCTTAAAGCTTTTTAGGATCCCAGATGAAAGATGCTACTGCAGTG<br>TAAAGTTCTAATATTATTTATTTCCCTAGTCATCAACATTAG |
| linc-P2RX4 [chr12 (121625339→ 121627249)] | [SEQ ID NO: 09]<br>TAGTATGTTTCTATCACCTTAATGAGGCCGCAGATGGAGTCAGAATGTGAAA<br>TTACAAATAATCACTGGATCCATCTACTGTTTTCCATCACCTTCCCCACTGATG<br>CTCTGGGCGAGAGAGTGATGTGTCACTTCAACTGTGTGTAATATGTCAGACA<br>CGTCCTACAATAACAGGCGTCATATTTGTATTATTTTTAGTTTACTGTAGAAAA<br>TAATGTCACCGCCAAAGGTGATGAGAGTCACGTTTTGTAGGATCTGTTTTCTT<br>ATACTTAAAGACAGACTTCTGCTACGGTAATTGCCAGTATTCATGGCTTCCTTT<br>CTGTGTCAGAAGAGAAGGGATCTGCTTTCTCTTGGCTGATTTCACATAGCATT<br>GGTAATAGACATGCATTTCTCTTTCTAAAGGGGAGTAACTTTTTAAACCCTTCC<br>TGATTTTAGCCTGGCAATGTAAGTGTCCTTAATGTGACTGTTTTGATAATTAA<br>AAAAAGGTATATAATTTATTTAAATCTTCATTTCCTTTCTTTTCAGAAGGTCCC<br>CAAATCACAGTTAACTCATTCATTGACGCATTCACTCAACAACTATTCAATGAG<br>GCACTCTCTAGAGACCAAGGATAAATAAGGTAGCCAGTCTCATAGAGATATG<br>AGGAGATGGAAATTAATCAAATAATTCAAGCAAATGGCATCTTGCAACTTGT<br>GCTGAGTATAATGGTGAAAAGGCAAATGATGGCATGAGAGCTTATAGTAGG<br>GAAATTTGGCCTATTTGGGGAGATCAGCCTACCTGAGGAAGGAATGTTTTAG<br>CTAAAATCTGAAGGATGAGTATTACTTAACTAGTGAATGCGGGAGGAAAGA<br>GCATTCTAGGCAGAGAACAGTATGTGCAAAGGTCCTGGGGCAGGAAAAGCA<br>GAGCAGGTTTATAGAACTTAAAGGAGAACTGTATGACTGTGCCATAAAAAGT<br>ACAGAGAAGTAAGGCATGAGTTACGGTTGGACAAGCAGGCAGGGGCTAGG<br>CTGCCTGGAGCCTGTGGGCCATGGTAGAGTTTGTCTGTATCCTAAGACCTAA<br>GCCACATAAGGGTTCTAAGCAGGAACCTGGTAAGATCACATTTAATTTTAATT<br>TTTTTATTTTTATTTTTATTTTTGAGATGGAGTCTTGCTTTGTTGCCCAGGCTGG<br>AGTGCAGTGGCTCAACCTCAGCTCACTGCAACCTCTGCCTCCTGGGTTCAATC<br>AATTCTCCTGCCTCAGCCTCCTGAGTAGCCAGGATTACATGTGTGCCACCATC<br>ACGCCTGGCTAATTTTTGTATTTTTAGTAGAGACGGAGTTTCTCCATGTTGGTC<br>AAACTGGTGCCGAATGCCTGACCTCAAGTGATTCACCAGCCTCGGCCTCCCAA<br>AGTGCTGGGATTACAGGAGTACGCCACAGCGCCCAGCCACCAAATTAATTTT<br>TAAAGATCACTATGATCGCTGTGTGGAAAATGAGCTGGGAGTGGTGGTGGA<br>TACAGTTTTTGTTTTTGTTTCAGTCTTTCCCTACTCCATGAAACATTTGCGCTAT<br>ATATGCGGCCAAATGGAATGTTTCTCTTTTCTCCCCTCCTCTTCCTCTTGGGAA<br>GTCACC |
| linc-CXorf36-3 [chrX (46182883→ 46187090)] | [SEQ ID NO: 10]<br>CCTGCCCACTGGGTGAAACTGCAAGTCGAGAGCGTGGGAAACCAGCAAGTT<br>GAGAGAGGATCCAGAAGTAACCCCTTCTAAAACGGGAAAGATGCCTTCCGAA<br>AGACCGGATGGCCTGGTACTGGTCTTCTCTAGACTGAAGGTCCTCCACCAGG<br>TCTCCTGCTGCTGCTACCTAAGAAAGAAATCTCACAAGGGTGTTAAAAGCACT<br>TGGCCCTAAAGAGAAAACACTAGGAGGATGGGAACCAGGGACAGAGAAGC<br>TACTTGCTCTGCAGCTGTTTGGGCCAATGATCCAATGGCCCCATCTAGACTGG<br>AGACACCAACTCATGACTCAGCTGGCCTTGTGGCCCACACCCAGAAGTGGAC<br>TCAGTGCATGAGGACTATTTTCCACACTCCTATGATAGCATCCCCAACCAATC<br>AGCAGGACCATTTCCTAGCCCCTTGCCCACCCAAACTATCTTTTAAAAACCTG<br>GCTGGGCGCAGTGGCTCACACCTGCAATCCCAGCACTTTGGGAGTCTGAGG |
| linc-CD180- 9: copy2 [chr5 (68322582→ 68325992)] | [SEQ ID NO: 11]<br>AGGCAACAGATGACTTTCTGCAAAGGCACTGATAATAGCTATGAGGAATAAA<br>TATTGCAGATGGATTAAATCAAAGAATCAAATTTCAAAGCCAAATTAGTCGTG<br>AAAAGGAGGGAGAAGCAGAAATGAAGAAAAAAGAACCACAGAAGTAAAAT<br>CAGCAGCATTGAAAAGAAAATCATCTGCTGTTTGAATAAAGACCCAAGATCTT<br>TCATTGTTGGATCCCCAAAGCCAGTGCCTTTTTTGAGCAGCAAGTCCCAAGAT<br>CAAGAAATCAGAAGGAACTAATACTTTAACTAATTAGTAGTAATGAAAATTTA |

TABLE 1-continued

| Gene ID [Chromosome location (start→stop)] | [SEQ ID NO.] Example DNA Sequence encoding the lincRNA |
|---|---|
| | CTAGACATCAATGACAAATTTACAAGGCAAATTTATTTCCAAAGTACATTCAT<br>ATATATCACAGGATCACTTCACTGAGGAACTGAACACGAGCATTTAACTTGTG<br>TGACTAGTTATGGCCTGGTCTGGATTTCCTTCTGGTTCTCAAGATGTCTTACAT<br>GAAAAAAGCTCTGTGGCACATTACATTTGGGAGCTGCTGATTAAAGACATAT<br>AAGCTCTTTTGCTGACCATTTTTCCAGAACCTTGACTGGAATGTTAATATCCAT<br>TGTAAATCTCTAAGTGGGTACCAGTGTTCTGCAAAGCACTCTGGGAAATGTTT<br>CCCTTTCCTTTATCTTTTTTAGCCAGTCCCAATGTATTATAACTTGAGTGAAAC<br>AGAGCTGTCCTATACGCCACTCTCAGCATACTGAGACATCCAAAGGAAATCCA<br>AGTCTGGCTGAAAAAATCACCCACCTTGAAAAACAACGTATGTTGATCAAGA<br>CAGATGCCTCTTGGAGAG |
| linc-ELMOD1 [chr11 (106120746→ 106133955)] | [SEQ ID NO: 12]<br>GTGGAATTATAAAACCTTTGGAAAATCTTTCATGTGAGAACAACATGGGGGC<br>AAGCCTCTGACCAAAATAGCTCAAAAATTTGTGTTACGCAGTTACAGTAAATA<br>CCCAAGAGCTTGACGCATAAAACACAACAGCCTCCTGGAGACAGAGGGAGG<br>AGAAAGAAAGATAAAGTCTGTGGCTTTAGAAGAAAAGGAATAACTTAAGAG<br>GCTTGTTTGCTGTTCAGGCTGGCCACCAAGGATGACATTTTGGATACTATAAG<br>AAGATTGGGATAGATACTGAGTGAGCCTCAGAAAATCAGCTGGATACACCCC<br>AGCTCCCTCCCACCACATGAACTAAAGATCTGCAAGCTGTAACCTTTTCCGAA<br>GGGCTACCTGGGCCTCTGTGTCCATCAGAGCTGATGAGCTGATCTTCATTCAC<br>CATAAGTGCAACTATCATGGCTCATGGAGCCCTGGAGAGAGTAGCACATATA<br>TTGAACTTCAGTTTTAAAAAGTCTAATACTTTTCTAAAATGACTTGCTATCTAT<br>TTCATCCAGAGAAGATTTATTACGTAGCCTTTCTAGCATAAAATATCATTACTT<br>TTAAAGAAAAATCCAATCTAAATTCCTCTAACTACAATGGAAGTCCCCTTTTCT<br>TATTCATTTCTCACTCAAATATGGAACAACCAGTCACTTCCATTAAATCTAATC<br>TTCCTGTATGCTCTTGAAGATAACTACCAGTTAAACAGAGCTATCTATGGGAA<br>TGGTTTTTGAAAAAAAATTGCGTTGTTTCAGTACTTTGGAGGATGGCTGATGT<br>TTGCCTTTTCAAGAGATGTATCATGGACTGTTTTTGTTAAACTAACTTGGCTTC<br>AAGAATTTGAGACTAACTCAGATTTTCTCAAACAGTGGGGGATTTGATGCAG<br>CAATATGCAGGCATGGGATATCAGAAAGAGCCAGATAACCAAAGGAAGAGT<br>AGTAGCTGAAGCAGGATTCTAAGACCAAGAAATCATTTTCATGCTGCATTACG<br>GTTGCCAGATTAGTCATTAAATAAACAGTATACAATTCATTGAACTCTCTGTTA<br>GCCCATTTGAAAGATGATGAAGTTAGAATGCTTAATATATGGTCCTTTGTGTT<br>TGGAGCAGATAAAAGCGTTCTGGAAAATTCCCAAGAGTAGAATATTAATTTC<br>AGGGCAGAAGAGATTTTGCTGTTTCGGTCGTGGCATTATCTCCAGTATTTAT<br>GTGCCTGGAACATATTAGTTGCCCATGCTTTGACGAGTGGGATGGCCCTTTG<br>AAGCAGAGACACACCTTTCTCCCTGGGTGCTACCTGAGCACTTCTTACAAAAC<br>CATTTGTTTTATTATGACATTTAGCGAGATTGTGTTATTTTTACTCACATGCCAA<br>ATGCTGTACTTCAATATGAGCTTTTCAAGAAGTAAAGAATAGTGAATTATTCC<br>TATTTGTAACACAGATATGAGCCACCAGGGGCAACTATATGCAAACTAAATT<br>GATAGCTATGAGGTCATAGTGTTGAACTGTTGTTGCGAATACTTCTCTCGTAG<br>ACACCCTGAGAAGTGATAGTGAGTTCATGCTAAAGCTACAGTCTAACTTTCTA<br>AAAAGAGTTGAAATTATCTCATATTTAACATTCTGTGAATTCCATGTCCAGAA<br>GAGTTCAGGGTTATCAATGCGGTATTTTCTCAAAATAGAACCACTCTGTTCTC<br>CAAGGACTTAAAATATAGAAGCCCAGGAAATATTCTGTCAGTTATTAAAAAT<br>GTCCACTAACACA |
| linc-LAMA1-1 [chr18 (9008804→ 9010215)] | [SEQ ID NO: 13]<br>GGACATGGAAATTTCTAGAAAGAAGGCGCAAGCAGGACACCGGCGATAAAA<br>AGTTCCCTTTGTAACCAGACCAGCTGAGACCAGTTACAAAGCCTACCCCAGGT<br>ATCCGACCAGATGACTTCAAAAAGACCTCAGGCTTCATTATAATCTAATTTCC<br>ATGCTAAATGACACTTCCACCAGTGTCATGACGGTTGCCAGTCCCCGTGACAA<br>TGACCAGAAGGAGCCATAAAAGGACAAAAACAAGGGAGCCCCTCATTCCAA<br>GAAGTGTACCGCCCAGTTCCAGAAAAGACATGGATATTCCTCCTCTTGCTTTT<br>AATGTCCAGCCATCATTAAGGAAACCCTATATGATAACCCCCTCACCCCTCACT<br>AATTGAGAAGTTGATTTGTGAGCCAAGCTCCCGCTTCTCAATTCCATGGCCAT<br>CGAATAAAG |
| linc-NUDCD2-3 [chr5 (166331944→ 166334981)] | [SEQ ID NO: 14]<br>CACATCCAGTACATGAATAAATGAAAAACGCAAGTTACAAAACATTACAGAG<br>GTAAAATCATAAATATAGTCCCTGAATTTCATGGCCACCTGACCTTCACATGA<br>AGCTCATATTAAAGCCATCTATAGAGCATGTTTTCCTGAAAACTTGACAAGTG<br>AGTACACACAACCTCTCTTTCTTTGGTCATGTGGAGATAGGAGTTTTGTACCA<br>TAAAAGGCATAGCCCAAAGTGTCAATTGTTAGCTCCCTAAGAGGCAGGCCC<br>ATGGTCGTCTTAAATGCCAGCAGCAGGTTGAAGTCACCTGGAATGGTGTTTC<br>AGAGAAATCCTCTTTAGTATAGGGAAGGCTTGTAGTCTGAGAAATCATTCCAT<br>GTTGGAATTGGGAATAAAGACAGTCCTCTCACCATCCT |
| Chromosome location 106120963→ 106134796 | [SEQ ID NO: 15]<br>TGTTCAGGCTGGCCACCAAGGATGACATTTTGCTGCAGCAGAGCCATCAGAA<br>AACAACTCCTGATTTTAGTTGATCAGATTCAAGTCAATGAAAAAATGACGTTT<br>CTGTGTGTCTACTTCGGGCTAAGCACCAGGGTAGGCACAAGAGAGATCACAG<br>GGATGAATTAGTCCTAGCCCCTTGGAGATTATCCTCTCACCCCTCTCCCCGCCAT<br>AGTTATCTTGGTCCTTTTCACATATATCTTAGCAGGTTCTGTTTCAGGCAAAGT<br>TTCACTTCTGTATATGTTTGTTACTACTGTTCATTTGAGATCTGCCACTAACCCT |

TABLE 1-continued

| Gene ID [Chromosome location (start→stop)] | [SEQ ID NO.] Example DNA Sequence encoding the lincRNA |
|---|---|
| | CATTATGACCTGGGACATGTCTGTGGCCCCTCCACATGCTGGCAGGATAAAA<br>ATTGACCAAATATATGATGCTGTCACATAGATGGATCCTATTATTTGGTGATT<br>ACATTGAAATCTTTACTGTAAAAATTGTGTTGTCAAAAATGAAAACAGATGAT<br>ACTGAGTAACTCACTAGTGCCCTAAAGTACTCTACAGCTTTTCAAACAAAATT<br>GAATATTCTTTTCAACATTCTCTCTGTAAAAAAAAAAAACAATTCTATATTAGT<br>GACCCTATATCCAAT |
| Chromosome location 9008811-9010367 | [SEQ ID NO: 16]<br>GATAAATTTGCACAGGGACAGATGCTCAGGGGAAAGGAAAGAGCTCTGCCT<br>TGCACTTGTACAGAAAGGAAACAAGGCAGCAGAGGCAAGACCAATGGAGAG<br>TACGGCAGCAAGACAGAAAGGGGCAGAAGGCGACAGAACATGCACGCTGG<br>GGACATGGAAATTTCTAGAAAGAAGGCGCAAGCAGAAACAGGACACCGGCG<br>ATAAAAAGTTCCCTTTGTAACCAGACCAGCTGAGACCAGTTACAAAGCCTACC<br>CCAGGTATCCGACCAGATGACTTCAAAAAGACCTCAGGCTTCATTATAATCTA<br>ATTTCCATGCTAAATGACACTTCCACCAGTGTCATGACGGTTGCCAGTCCCCG<br>TGACAATGACCAGAAGGAGCCATAAAAGGACAAAAACAAGGGAGCCCCTCA<br>TTCCAAGAAGTGTACCGCCCAGTTCCAGAAAAGACATGGATATTCCTCCTCTT<br>GCTTTTAATGTCCAGCCATCATTAAGGAAACCCTATATGATAACCCCCTCACCC<br>CTCACTAATTGAGAAGTTGATTTGTGAGCCAAGCTCCCGCTTCTCAATTCCAT<br>GGCCATCG |
| linc-USP14-3 [chr18 (11124→16421)] | [SEQ ID NO: 17]<br>AGGCGCAGGCGCGGAGGGGCGCGCCCGAACCCGAACCCTAATGCCGTCATA<br>AGAGCCCTAGGGAGACCTTAGGGAACAAGCATTAAACTGACACTCGATTCTG<br>TAGCCGGCTCTGCCAAGAGACATGGCGTTGCGGTGATATGAGGGCAGGGGT<br>CATGGAAGAAAGCCTTCTGGTTTTAGACCCACAGGAAGATCTGTGACGCGCT<br>CTTGGGTAGAGCACACGTTGCTGGGCGTGCGCTTGAAAAGAGCCTAAGAAG<br>AGGGGGCGTCTGGAAGGAACCGCAACGCCAAGGGAGGGTGTCCAGCCTTCC<br>CGCTTCAACACCTGGACACATTCTGGAAAGTTTCCTAAGAAAGCCAGAAAAA<br>TAATTTAAAAAAAAATCCAGAGGCCAGACGGGCTAATGGGGCTTTACTGCGA<br>CTATCTGGCTTAATCCTCCAAACAACCTTGCCATACCAGCCCATCAGTCCTCTG<br>AGACAGGCAAGCCCAAGAAAGTCAGGGGCCTATGTGAGCCAAAGAGGAGA<br>GAAGGTGATGCCTCAGCCCAGTGTTTCTGCCCCACCTCGCTTGTGGCCTTCGG<br>AACTTGATTTGCACCGCAGGAAAATGGGCAATGAAAACCCCTCCCTAACTGG<br>CTTCTCAGTCCACTCTGACCAGCCCACTGCACAGCGCCCACCCTGCAGCTCCA<br>GATGAGGCCTCACTCTGTCACCCAGGTTGGGGTGGAGTGGCACAGTCACAGC<br>TCACTATAACCTCAAGCTCCTGGGCTCAAGTGATCCTGCCACCTCAGCCTCCT<br>AAGTAGCTGGAACTACAGATGTGCACTGCCATGCCAGGCTTGTCTAACATTTT<br>TATGTGTTGCTTCATCCAGTTTGCTAGAGTTTTTGGAGATTTCTGTCTTCATTC<br>ATGAGGGATAATAGTCTGCACTTTTATTTTCTTGTGATACTTTTGTCTGATTTG<br>TTATCTGGGTAATACTGGCCTTGAAAATGAATTGATGTTTTCCTGCTTCTCTGC<br>TTTGCAAGTGTTTGTGAAGGATTGGTTATTCATTAAGTGTTTAATAGAATTCA<br>CTAGTGAAGCTATGTGAGCCAGGGCTAGACTGATGAAGAGTTTTCATTAGTC<br>TAATCTGTTTACTTGCTGTATAAGTACGCATATATTCTCTTTCTTCTTGATTTAA<br>TTTTACACTTTGTGTATAGCAGGGAATCTGTGTCTAATTTGTAGTATTTCATGC<br>TTCTAGGTTTTCATGGCAGTTGAGATGTAAGAATAACAATAATGTTGGGAGA<br>AGGAAGTTGTGGACAATCCATGAATATCCCAACATCTGTTGTAGGAAGGTTA<br>AGATTACTTTTTTTTTTTTGCTGTACTGAACTGAATACTCTTATTTATAATGTC<br>AGACAAATGTAATGTTGTATATAAATAGAACTAGGAAAATGTGCCATTTGTCT<br>TAGTATTTAATCAAGATGGAAGTCTGGGCCTACCTCCTCTCTTTTATTAATATG<br>TAGACA |

Exemplary methods to determine and/or detect the presence or absence of a lincRNA in a sample can include isolating RNA from a sample, such as a serum sample. In some embodiments, an RNA library can be prepared from the isolated RNA. In some embodiments, the presence or absence of a lincRNA can be determined by hybridizing a probe to the isolated RNA. In some embodiments, a hybridized probe can be extended and the sequence of a lincRNA in a sample can be determined. In some embodiments, a hybridized probe can be indicative of the presence of a lincRNA in a sample. In some embodiments the probe comprises a nucleic acid. In some embodiments, a probe comprises a nucleic acid capable of hybridizing to a target nucleic acid or a complement thereof, in which the target nucleic acid comprises a sequence of SEQ ID NO: 1-17, or a fragment thereof.

In some embodiments, a sample, such as a serum sample, can be enriched for exosomes. Examples methods that can be used to enrich for exosomes include ultracentrifugation, density gradient separation, and ultrafiltration. See. e.g., Sharma S., et al., (2018) Methods Mol Biol. 1710:103-115; and U.S. 20180224465 which are each incorporated by reference in its entirety. In some embodiments, a sample can be further enriched for exosomes comprising CD31. Examples of methods to enrich for exosomes comprising CD31 include affinity methods such as contacting a sample comprising exosomes with an anti-CD31 antibody or antigen binding fragment thereof. In some embodiments, the anti-CD31 antibody or antigen binding fragment thereof can be attached to a substrate, such as a bead, a membrane, a slide, a gel, or a microwell plate, or other substrate described herein.

Some embodiments also include determining and/or detecting the presence or absence of an additional KD biomarker in a sample, such as a serum sample. In some such embodiments, the additional KD biomarker can include a microRNA. Example microRNAs are listed in TABLE 2. Some embodiments include determining and/or detecting the presence or absence of at least 1, 2, 3, 4, 5, or any one of the foregoing numbers, of microRNAs in a sample, such as a microRNA listed in TABLE 2.

TABLE 2

| microRNA | SEQ ID NO | Example Sequence |
|---|---|---|
| hsa-miR-3116-1 | 18 | UGCCUGGAACAUAGUAGGGACU |
| hsa-miR-576-5p | 19 | AUUCUAAUUUCUCCACGUCUUU |
| hsa-miR-766 | 20 | AGGAGGAAUUGGUGCUGGUCUU |
| hsa-miR-339-3p | 21 | UGAGCGCCUCGACGACAGAGCCG |
| hsa-miR-4510 | 22 | UGAGGGAGUAGGAUGUAUGGUU |

Some embodiments of the methods and compositions provided herein include diagnosis of a subject having KD. Some such embodiments can include determining and/or detecting the presence or absence of a KD biomarker, such as a lincRNA, in a sample from a subject as described herein. In some embodiments the presence of a lincRNA in the sample can be indicative of a subject having KD. Examples of a lincRNA that can be indicative of a subject having KD include at least one of lincRNAs include linc-MBOAT7, linc-ZNF337-1, linc-RBM45-2, linc-WDR7-5, linc-CISD1, linc-ADARB2-2, linc-COBL-2, linc-NPVF-2, linc-P2RX4, linc-CXorf36-3, linc-CD180-9:copy2, linc-ELMOD1, linc-LAMA1-1, and/or linc-NUDCD2-3.

Some embodiments include determining and/or detecting the presence or absence of an additional KD biomarker, such as a microRNA, in a sample from a subject as described herein. In some embodiments, the presence of a microRNA in a sample can be indicative of a subject having KD. For example, the presence of a microRNA such as hsa-miR-3116-1, hsa-miR-576-5p, and/or hsa-miR-766 in a sample can be indicative of a subject having KD. In some embodiments, the absence of a microRNA in a sample can be indicative of a subject having KD. For example, the absence of a microRNA such as miR-339-3p, and/or hsa-miR-4510, in a sample can be indicative of a subject having KD.

Some embodiments of the methods and compositions provided herein include ameliorating or treating a subject having KD. As used herein, "treat," "treatment," or "treating," can include administering a pharmaceutical composition to a subject for therapeutic purposes, and can include reducing the symptoms or consequences of a disorder, such as KD. As used herein, "ameliorate", or "ameliorating" can include a therapeutic effect which relieves, to some extent, one or more of the symptoms of a disorder. As used herein, an "effective amount" can include an amount, such as a dose, of a therapeutic compound sufficient to treat a disorder. Some embodiments can include determining and/or detecting the presence or absence of a KD biomarker, such as a lincRNA and/or microRNA, in a sample from a subject as described herein. Some embodiments can include diagnosing a subject having KD as described herein. Some embodiments include administering a therapy to treat the KD to the diagnosed subject. In some embodiments, the therapy can include an effective amount of a composition, such as intravenous immunoglobulin, aspirin, and a corticosteroid.

Kits

Some embodiments of the methods and compositions provided herein include kits for detecting a vasculopathy, such as KD in a subject. In some embodiments a kit can include a probe adapted to detect the presence of a KD biomarker in a sample, such as a long intergenic non-coding RNA (lincRNA). In some embodiments, the probe can include a nucleic acid, such as a primer. In some embodiments, the primer can be attached to a first substrate, such as a bead, a membrane, a slide, a flow cell, and/or a microwell plate. In some embodiments, the probe is adapted to detect a lincRNA, such as at least one of linc-MBOAT7, linc-ZNF337-1, linc-RBM45-2, linc-WDR7-5, linc-CISD1, linc-ADARB2-2, linc-COBL-2, linc-NPVF-2, linc-P2RX4, linc-CXorf36-3, linc-CD180-9:copy2, linc-ELMOD1, linc-LAMA1-1, and/or linc-NUDCD2-3. In some embodiments, the probe is capable of hybridizing to a nucleic acid sequence of any one of SEQ ID NOs: 1-14 or a complement thereof.

In some embodiments, a kit can include an additional probe adapted to detect the detect the presence in a sample of a KD biomarker comprising a microRNA, such as at least one of hsa-miR-3116-1, hsa-miR-576-5p, hsa-miR-766, hsa-miR-339-3p, and/or hsa-miR-4510.

In some embodiments, a kit can include an anti-CD31 antibody or fragment thereof. In some embodiments, the anti-CD31 antibody or fragment thereof is attached to a substrate, such as a bead, a membrane, a slide, a gel, a flow cell, or a microwell plate.

Methods for Identifying Kawasaki Disease Biomarkers

Some embodiments of the methods and compositions provided herein include methods to identify biomarkers for KD. In some embodiments, exosomes comprising a marker for an endothelial cell, such as CD31, CD105, or CD146, can be isolated from a subject having KD, and a control subject not having KD. The contents of the isolated exosomes can be analyzed, and differences between the isolated exosomes from a subject having KD, and the isolated exosomes from a control subject can be identified.

EXAMPLES

Example 1

Identification of Kawasaki Disease (KD) in Patients

Samples were assessed from 5 patients with KD, and from 5 age-matched control individuals. In initial studies, exosomes were analyzed expressing CD31 (also known as PECAM-1), a protein or antigen that is highly expressed on and unique for the surface of endothelial cells. Analysis of CD31-positive and CD31-negative exosomes that had been isolated from serum samples collected from 5 patients diagnosed with KD (prior to their being exposed to intravenous gamma globulin [IVIG]) and from a control group of 5 age-matched children with febrile illnesses other than KD demonstrated that, although the two groups did not substantially differ in RNA expression within the CD31-negative exosomes, there were numerous long intervening non-coding RNAs (linc-RNAs) expressed in KD patients' CD31-positive exosomes that were entirely absent in the control CD31-positive exosomes. Additionally, multiple micro-RNAs and linc-RNAs showed markedly different quantitative expression patterns between KD and control CD31-positive exosomes. These data indicate CD31-positive exosomes contain unique RNA markers, and RNA expression patterns among patients with KD, and these markers and patterns (or their subparts) serve as specific biomarkers for the disease.

Methods for obtaining and analyzing the RNA are illustrated in FIG. 1, and included serum collection (110), exosome isolation (120), CD31 exosome isolation (130), exosome RNA preparation (140), and exosome library construction (150). After RNA library construction, the RNA was analyzed for markers and specific patterns. Specifically, serum was isolated from 5 patients with KD and 5 age-matched children with febrile illness other than KD. Exosomes were isolated from the serum and CD31+ exosomes were collected using CD31 antibody-coupled magnetic beads. RNA was extracted from the isolated exosomes and RNA-sequencing libraries were constructed using modified Illumina adapter methods and index with separate bar codes for multiplex sequencing. Sequencing was performed using an Illumina MiSeq v3 instrument and the 2×75 bp paired-end run setting. As shown in the table, the data represent intensity reads (or level of expression) of the designated linc RNAs after normalization to a specific control RNA. Zero (0) represents no expression.

TABLE 3 lists linc-RNAs unique for CD-31+ exosomes from sera derived from acute Kawasaki disease samples. Each sample was from a different KD patient. All control samples from healthy children with other febrile illnesses (1-5) had readings of zero (0) for all linc-RNAs listed in TABLE 3. CD31 positive exosomes in KD subjects included lincRNAs: linc-MBOAT7, link-ZNF337-1, linc-RBM45-2, linc-WDR7-5, linc-CISD1, linc-ADARB2-2, linc-COBL-2, linc-NPVF-2, linc-NPVF-2, linc-P2RX4, linc-CXorf36-3, linc-cd180-9:copy2, linc-ELMOD1, linc-LAMA1-1 and linc-NUDCD2-3.

TABLE 3

| Gene ID | Signal level in sample | | | | | Median signal |
|---|---|---|---|---|---|---|
| | 1 | 2 | 3 | 4 | 5 | |
| linc-MBOAT7 | 2 | 14 | 1 | 1 | 34 | 2 |
| linc-ZNF337-1 | 2 | 123 | 35 | 29 | 0 | 29 |
| linc-RBM45-2 | 1 | 56 | 53 | 10 | 0 | 10 |
| linc-WDR7-5 | 0 | 1 | 2 | 11 | 3 | 2 |
| linc-CISD1 | 0 | 1 | 2 | 5 | 4 | 2 |
| linc-ADARB2-2 | 63 | 1 | 1 | 0 | 2 | 1 |
| linc-COBL-2 | 1 | 4 | 2 | 1 | 0 | 1 |
| linc-NPVF-2 | 3 | 1 | 4 | 0 | 1 | 1 |
| linc-P2RX4 | 54 | 1 | 1 | 0 | 6 | 1 |
| linc-CXorf36-3 | 54 | 1 | 0 | 10 | 1 | 1 |
| linc-CD180-9:copy2 | 54 | 1 | 2 | 0 | 1 | 1 |
| linc-ELMOD1 | 55 | 1 | 95 | 1 | 0 | 1 |
| linc-LAMA1-1 | 85 | 1 | 1 | 1 | 0 | 1 |
| linc-NUDCD2-3 | 1 | 0 | 1 | 36 | 1 | 1 |

Figure 2:
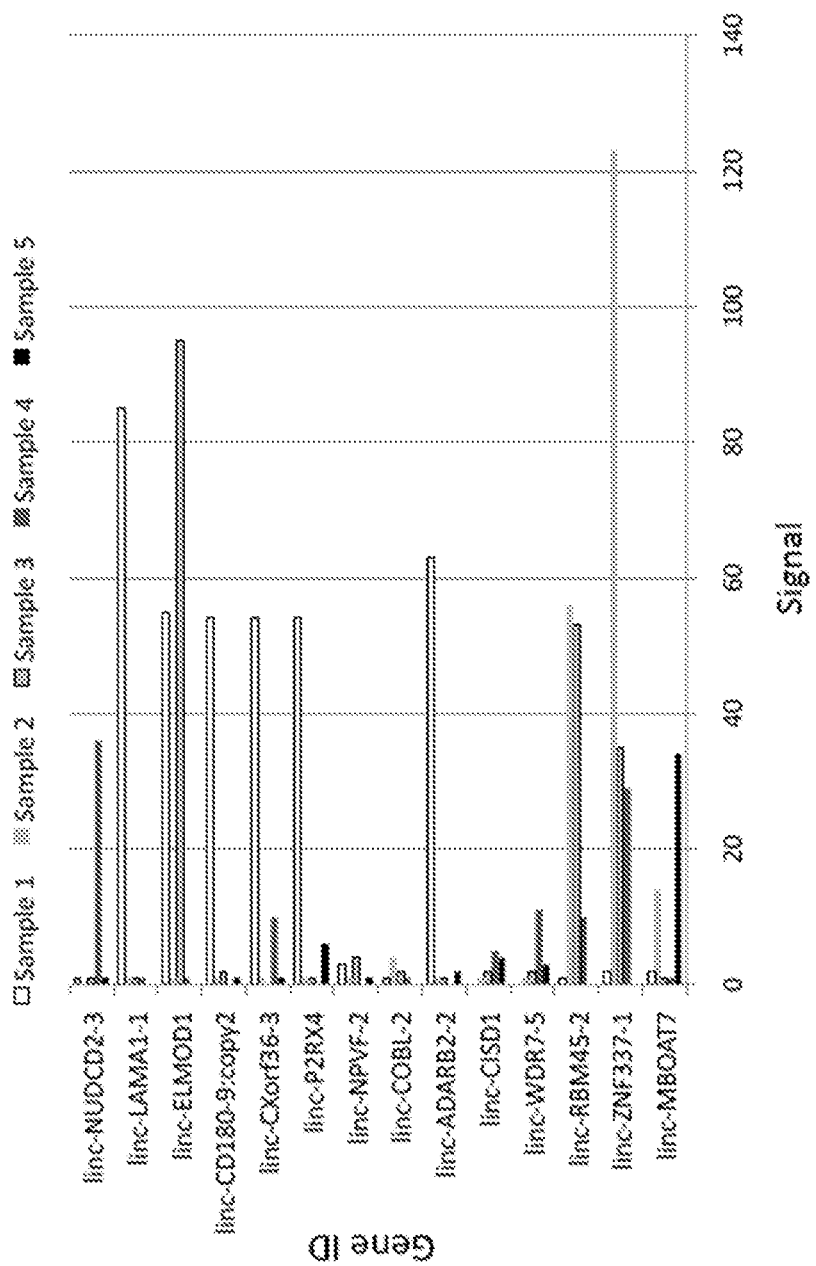
FIG. 2 is a graph depicting the level of signal for certain linc RNA markers in various samples and grouped by linc RNA marker, and illustrates data listed in TABLE 3.
Figure 3:
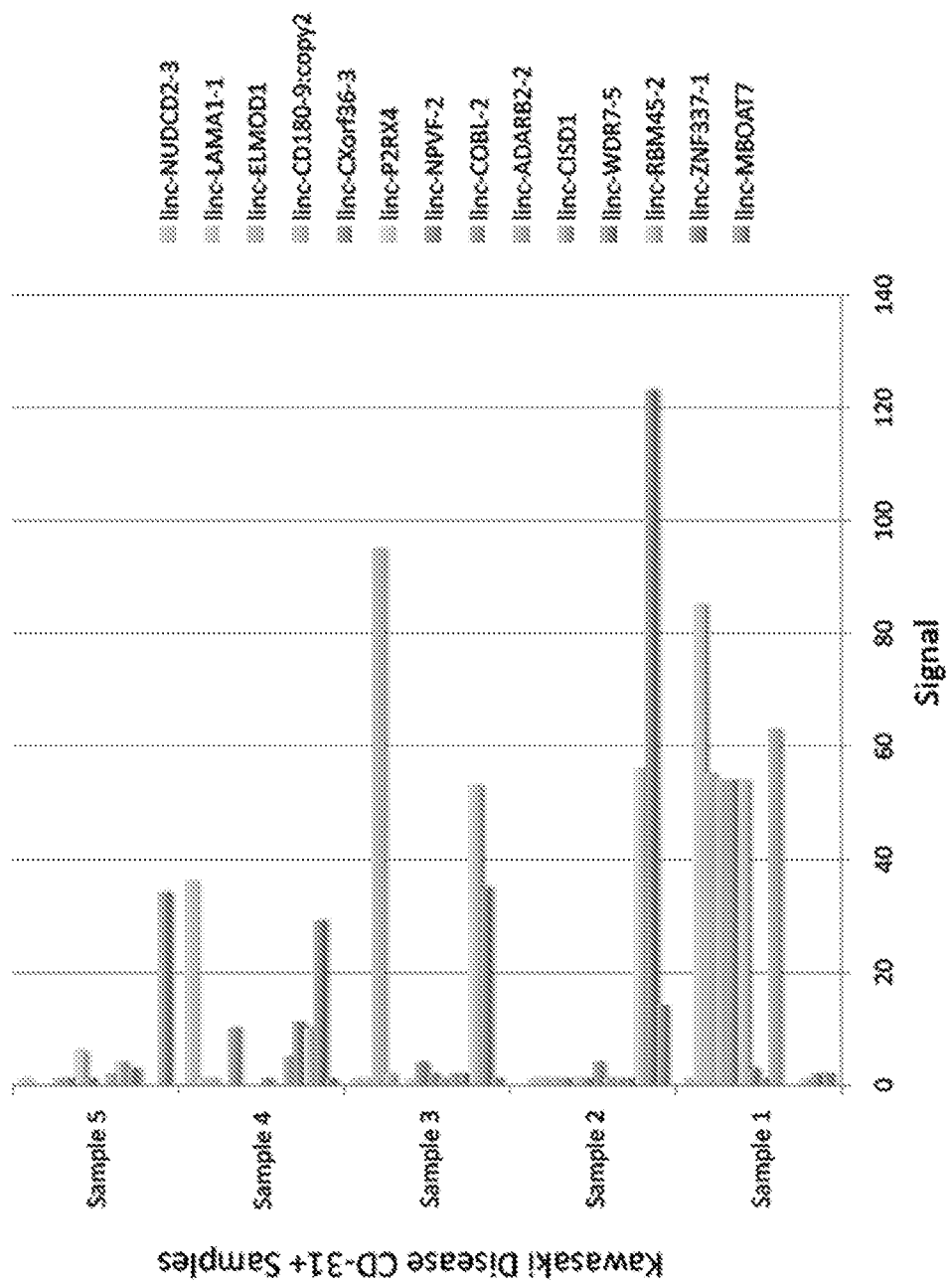
FIG. 3 is a graph depicting the level of signal for certain linc RNA markers in various samples and grouped by sample, and illustrates data listed in TABLE 3.

FIG. 2 illustrates the data presented in TABLE 3 grouped by lincRNA. FIG. 3 illustrates the data presented in TABLE 3 grouped by patient sample. TABLE 1 lists example DNA sequences that encode lincRNAs of TABLE 3.

Example 2

Nanoparticle Characterization Data

To study the exosomes and concentrations of particles in various patient samples, serum was isolated from 5 patients with KD and 5 age-matched children with febrile illness other than KD. Exosomes were isolated from the serum and CD31+ exosomes were collected using CD31 antibody-coupled magnetic beads. Unbound exosomes and eluted bead-bound exosomes were analyzed using a Nanoparticle Tracking Analysis (NTA, Malvern Instruments) to determine particle size and concentration. Results of the experiment are shown in TABLE 4 which lists exosome sizes and concentration of exosomes in samples. from patients.

TABLE 4

| Sample | Exosome size (nm) | Exosome concentration (particles/ml) |
|---|---|---|
| KD1-UB | 97 | 2.49E+11 |
| KD2-UB | 104 | 3.43E+11 |
| KD3-UB | 100 | 2.47E+11 |
| KD4-UB | 101 | 4.29E+11 |
| KD5-UB | 93 | 2.53E+11 |
| C1-UB | 111 | 6.42E+11 |
| C2-UB | 104 | 3.42E+10 |
| C3-UB | 85 | 1.05E+11 |
| C4-UB | 90 | 4.69E+10 |
| C5-UB | 103 | 8.71E+10 |
| KD1-Elu | 118 | 1.34E+09 |
| KD2-Elu | 96 | 8.46E+09 |
| KD3-Elu | 88 | 4.55E+09 |
| KD4-Elu | 97 | 6.83E+09 |
| KD5-Elu | 80 | 6.36E+09 |
| C1-Elu | 78 | 6.16E+09 |
| C2-Elu | 103 | 2.31E+09 |
| C3-Elu | 101 | 4.78E+09 |
| C4-Elu | 98 | 1.23E+10 |
| C5-Elu | 102 | 5.55E+09 |

KD = exosomes isolated from KD patient.
C = exosomes isolated from control samples.
UB = unbound (exosomes not bound to CD31antibody-conjugated beads).
Elu = eluated (exosomes eluted from CD31antibody-conjugated beads.

Example 3

MicroRNAs Extracted from CD31 Positive Exosomes of KD Patients

Serum was isolated from 5 patients with KD and 5 age-matched children with febrile illness other than KD. Exosomes were isolated from the serum and CD31+ exosomes were collected using CD31 antibody-coupled magnetic beads. RNA was extracted from the isolated exosomes and RNA-sequencing libraries were constructed using modified Illumina adapter methods and index with separate bar codes for multiplex sequencing. Sequencing was performed using an Illumina MiSeq v3 instrument and the 2×75 bp paired-end run setting. Data shown represent intensity reads (or level of expression) for microRNAs found to be unique to either CD31+ KD exosomes or CD31+ exosomes from controls after normalization to a specific control RNA. Zero (0) represents no expression. As shown, TABLE 5 lists MicroRNA derived from CD31 positive exosomes of acute Kawasaki Disease patients, each sample was from a different donor.

TABLE 5

| | Gene ID | KD1 | KD2 | KD3 | KD4 | KD5 | C1 | C2 | C3 | C4 | C5 |
|---|---|---|---|---|---|---|---|---|---|---|---|
| KD-unique | hsa-miR-3116-1 | 0 | 9 | 1 | 0 | 2 | 0 | 0 | 0 | 0 | 0 |
| | hsa-miR-576-5p | 1 | 0 | 102 | 0 | 0 | 0 | 0 | 0 | 0 | 0 |
| | hsa-miR-766 | 1 | 0 | 0 | 57 | 0 | 0 | 0 | 0 | 0 | 0 |
| Control-unique | hsa-miR-339-3p | 0 | 0 | 0 | 0 | 0 | 0 | 137 | 11 | 0 | 1 |
| | hsa-miR-4510 | 0 | 0 | 0 | 0 | 0 | 0 | 2 | 3 | 2 | 0 |

The microRNAs, hsa-miR-3116-1, hsa-miR-576-5p, and hsa-miR-766 were detected in KD patients, and were not detected in non-KD patients. The microRNAs, hsa-miR-339-3p, and hsa-miR-4510 were detected in non-KD patients, and were not detected in KD patients.

The term "comprising" as used herein is synonymous with "including," "containing," or "characterized by," and is inclusive or open-ended and does not exclude additional, unrecited elements or method steps.

The above description discloses several methods and materials of the present invention. This invention is susceptible to modifications in the methods and materials, as well as alterations in the fabrication methods and equipment. Such modifications will become apparent to those skilled in the art from a consideration of this disclosure or practice of the invention disclosed herein. Consequently, it is not intended that this invention be limited to the specific embodiments disclosed herein, but that it cover all modifications and alternatives coming within the true scope and spirit of the invention.

All references cited herein, including but not limited to published and unpublished applications, patents, and literature references, are incorporated herein by reference in their entirety and are hereby made a part of this specification. To the extent publications and patents or patent applications incorporated by reference contradict the disclosure contained in the specification, the specification is intended to supersede and/or take precedence over any such contradictory material.

What is claimed is:

1. A method for treating, inhibiting or ameliorating Kawasaki disease (KD) in a human subject, comprising:
   (i) detecting a KD biomarker in a biological sample from a human subject comprising:
      (a) providing a population of nucleic acids prepared from the biological sample, wherein the biological sample is enriched for CD31+ exosomes,
      (b) hybridizing a probe with the population of nucleic acids, wherein the probe is capable of detecting linc-ZNF337-1, and
      (c) detecting the presence of linc-ZNF337-1 in the biological sample,
      (d) identifying the subject as having KD when linc-ZNF337-1 is present; and
   (ii) administering a therapy for the KD to the subject having KD, wherein the therapy comprises an effective amount of a composition selected from the group consisting of an intravenous immunoglobulin, aspirin, and a corticosteroid.

2. The method of claim 1, wherein step (b) further comprises detecting the presence of an additional KD biomarker indicative of the subject having KD, wherein the additional KD biomarker is selected from the group consisting of linc-MBOAT7, linc-RBM45-2, linc-WDR7-5, linc-CISD1, linc-ADARB2-2, linc-COBL-2, linc-NPVF-2, linc-P2RX4, linc-CXorf36-3, linc-CD180-9:copy2, linc-ELMOD1, linc-LAMA1-1, and linc-NUDCD2-3.

3. The method of claim 2, wherein the additional KD biomarker comprises linc-RBM45-2.

4. The method of claim 2, wherein step (b) comprises detecting the presence of at least three additional KD biomarkers.

5. The method of claim 2, wherein step (b) comprises detecting the presence of at least five additional KD biomarkers.

6. The method of claim 2, wherein step (b) comprises contacting a probe with the population of nucleic acids, wherein the probe is capable of hybridizing with a target nucleic acid comprising the nucleotide sequence of any one of SEQ ID NOs:01, 03-14, or a complement thereof.

7. The method of claim 1, wherein step (b) further comprises detecting the presence of an additional KD biomarker indicative of the subject having KD, wherein the additional KD biomarker is selected from hsa-miR-3116-1 or hsa-miR-766.

8. The method of claim 7, wherein step (b) comprises detecting the presence of at least two additional KD biomarkers.

9. The method of claim 1, wherein step (b) further comprises detecting the absence of an additional KD biomarker selected from hsa-miR-339-3p, and hsa-miR-4510, and wherein the absence of the additional KD biomarker is indicative of the subject having KD.

10. The method of claim 1, further comprising contacting a serum sample from the subject with an anti-CD31 antibody or antigen binding fragment thereof to obtain the biological sample.

11. The method of claim 10, wherein the anti-CD31 antibody or antigen binding fragment thereof is attached to a substrate selected from the group consisting of a bead, a membrane, a slide, a gel, and a microwell plate.

12. The method of claim 1, wherein the probe is capable of hybridizing with a target nucleic acid having the nucleotide sequence of SEQ ID NO:02 or a complement thereof.

13. The method of claim 1, wherein the subject is a pediatric subject.

14. The method of claim 1, wherein step (a) further comprises enriching a serum sample from the subject for CD31+ exosomes to obtain the biological sample.

15. The method of claim 1, wherein step (a) further comprises preparing a nucleic acid library from RNA polynucleotides of the biological sample to obtain the population of nucleic acids.

16. The method of claim 1, wherein step (b) comprises sequencing the population of nucleic acids.

17. A method for treating, inhibiting or ameliorating Kawasaki disease (KD) in a human subject, comprising:
(i) identifying a human subject having KD, comprising:
(a) obtaining a library of nucleic acids prepared from RNA polynucleotides of a biological sample from the subject, wherein the biological sample is enriched for CD31+ exosomes,
(b) sequencing the library of nucleic acids,
(c) determining the presence of a nucleotide sequence of a KD biomarker in the library of nucleic acids, wherein the KD biomarker comprises linc-ZNF337-1,
(d) identifying the human subject as having KD when linc-ZNF337-1 is present in the biological sample; and
(ii) administering a therapy for the KD to the subject having KD, wherein the therapy comprises an effective amount of a composition selected from the group consisting of an intravenous immunoglobulin, aspirin, and a corticosteroid.

18. The method of claim 17, further comprising determining the presence of a nucleotide sequence of an additional KD biomarker in the library of nucleic acids, wherein the additional KD biomarker is selected from the group consisting of linc-MBOAT7, linc-RBM45-2, linc-WDR7-5, linc-CISD1, linc-ADARB2-2, linc-COBL-2, linc-NPVF-2, linc-P2RX4, linc-CXorf36-3, linc-CD180-9:copy2, linc-ELMOD1, linc-LAMA1-1, linc-NUDCD2-3, hsa-miR-3116-1, and hsa-miR-766.

* * * * *